United States Patent
Lind et al.

(10) Patent No.: US 11,846,635 B2
(45) Date of Patent: Dec. 19, 2023

(54) MAGNETIC IMMUNOGLOBULIN-BINDING PARTICLES

(71) Applicant: GE Healthcare Bio-Sciences AB, Uppsala (SE)

(72) Inventors: Ola Lind, Uppsala (SE); Klaus Gebauer, Uppsala (SE); Eric Faldt, Uppsala (SE); Nils Norrman, Uppsala (SE); Ronnie Palmgren, Uppsala (SE); Jesper Hedberg, Uppsala (SE); Niklas Jungnelius, Uppsala (SE); Karl Liderfelt, Uppsala (SE); Anita Solbrand, Uppsala (SE)

(73) Assignee: CYTIVA SWEDEN AB, Uppsala (SE)

( * ) Notice: Subject to any disclaimer, the term of this patent is extended or adjusted under 35 U.S.C. 154(b) by 1209 days.

(21) Appl. No.: 16/470,677

(22) PCT Filed: Dec. 21, 2017

(86) PCT No.: PCT/EP2017/084033
§ 371 (c)(1),
(2) Date: Jun. 18, 2019

(87) PCT Pub. No.: WO2018/122089
PCT Pub. Date: Jul. 5, 2018

(65) Prior Publication Data
US 2019/0339261 A1    Nov. 7, 2019

(30) Foreign Application Priority Data

Dec. 28, 2016  (GB) ................................. 1622304
Dec. 28, 2016  (GB) ................................. 1622305
Dec. 28, 2016  (GB) ................................. 1622307

(51) Int. Cl.
*G01N 33/543*       (2006.01)
*C12M 3/00*         (2006.01)
(Continued)

(52) U.S. Cl.
CPC ... *G01N 33/54326* (2013.01); *B01D 21/0009* (2013.01); *B03C 1/30* (2013.01);
(Continued)

(58) Field of Classification Search
CPC .......... G01N 33/54326; G01N 2333/31; B03C 5/02; B03C 1/01; C12M 23/14;
(Continued)

(56) References Cited

U.S. PATENT DOCUMENTS 6,471,860 B1    10/2002  Miltenyi et al.
2005/0019755 A1  1/2005  Marchessault et al.
(Continued)

FOREIGN PATENT DOCUMENTS

CN    103450328 A    12/2013
CN    104475041 A    4/2015
(Continued)

OTHER PUBLICATIONS

Kaeppler et. al., In Situ Magnetic Separation for Extracellular Protein Production. J. Biotech. and Bioeng. 2008; 105: 579-585 (Year: 2008).*

(Continued)

*Primary Examiner* — Gailene Gabel
(74) *Attorney, Agent, or Firm* — Eversheds Sutherland (US) LLP

(57) ABSTRACT

The invention discloses an immunoglobulin-binding magnetic bead, comprising a porous matrix and one or more magnetic particles embedded in said matrix, wherein said matrix comprises a porous polymer and at least 10 mg/ml Fc-binding proteinaceous ligands covalently coupled to said porous polymer.

25 Claims, 19 Drawing Sheets
Specification includes a Sequence Listing.

(51) Int. Cl.
| | |
|---|---|
| *C12M 3/06* | (2006.01) |
| *C12M 1/00* | (2006.01) |
| *C12M 1/34* | (2006.01) |
| *C12N 13/00* | (2006.01) |
| *B03C 5/00* | (2006.01) |
| *B03C 5/02* | (2006.01) |
| *B01D 21/00* | (2006.01) |
| *B03C 1/30* | (2006.01) |
| *B03C 1/01* | (2006.01) |
| *B03C 1/28* | (2006.01) |

(52) U.S. Cl.
CPC ............... *B03C 5/00* (2013.01); *B03C 5/02* (2013.01); *C12M 23/48* (2013.01); *C12M 27/16* (2013.01); *C12M 29/00* (2013.01); *C12M 41/44* (2013.01); *C12M 45/07* (2013.01); *C12M 47/04* (2013.01); *C12M 47/10* (2013.01); *C12N 13/00* (2013.01); *G01N 33/5436* (2013.01); *B03C 1/01* (2013.01); *B03C 1/288* (2013.01); *B03C 2201/26* (2013.01); *G01N 2333/31* (2013.01)

(58) Field of Classification Search
CPC ...... C12M 23/48; C12M 27/16; C12M 29/00; C12M 41/44; C12M 47/10
See application file for complete search history.

(56) References Cited

U.S. PATENT DOCUMENTS

| | | | |
|---|---|---|---|
| 2013/0143313 A1 | 6/2013 | Niazi | |
| 2013/0244322 A1* | 9/2013 | Henon | ............... C12M 27/16 435/325 |
| 2014/0329995 A1* | 11/2014 | Johansson | .......... B01D 15/3809 530/387.9 |
| 2016/0184737 A1 | 6/2016 | Oscarsson et al. | |

FOREIGN PATENT DOCUMENTS

| | | | |
|---|---|---|---|
| CN | 105418730 A | 3/2016 | |
| JP | 2011105679 A | 6/2011 | |
| JP | 2014161831 A | 9/2014 | |
| KR | 20150073282 A | 7/2015 | |
| WO | 20060010584 A1 | 2/2006 | |
| WO | 2006/112771 A1 | 10/2006 | |
| WO | 2007/050017 A1 | 5/2007 | |
| WO | 2009/102258 A1 | 8/2009 | |
| WO | WO-2011059512 A1 * | 5/2011 | ........ B01L 3/502753 |
| WO | 20150176018 A1 | 2/2015 | |
| WO | 2015/034428 A1 | 3/2015 | |
| WO | WO-2015034428 A1 * | 3/2015 | ......... B01D 15/3885 |

OTHER PUBLICATIONS

Cao et, al., (Immobilization *Staphylococcus* Protein A on Magnetic cellulose microspheres for IgG affinity purification. Artif. Cells Nanomed. Biotechnol. 80:5, 467-4, 2009). (Year: 2009).*
Holschuh and Schwaemmle (Preparative Purification of Antibodies with Protein A—An Alternative to Conventional Chromatography. J. of Magnetism and Magnetic Materials 293 (2005) 345-348) (Year: 2005).*
PCT International Search Report and Written Opinion for PCT Application No. PCT/EP2017/084033 dated May 3, 2018 (19 pages).
Great Britain Search Report for GB Application No. 1622305.9 dated Oct. 30, 2017 (7 pages).
Great Britain Search Report for GB Application No. 1622304.2 dated Nov. 9, 2017 (9 pages).
Andritz High-Gradient Magnetic Separator, 2017, 6 pages.
Ebeler et al., "One-Step Integrated Clarification and Purification of a Monoclonal Antibody Using Protein A Mag Sepharose Beads and a cGMP-Compliant High-Gradient Magnetic Separator," New Biotechnology, 2018, 42:48-55.
Flickinger, "Downstream Industrial Biotechnology; Recovery and Purification," XP055457932, 2013, 4 pages.
Franzreb et al., "Protein Purification Using Magnetic Adsorbent Particles," Appl. Microbiol. Biotechnol., 2006, 70:505-516.
GE Healthcare, 2009, "Mag Sepharose," https://www.gelifesciences.com/gehcls_images/GELS/Related%20Content/Files/1314787424814/litdoc28953763_20161014190437.pdf (2017).
Dhadge et al., "Magnetic Purification of Antibodies," 2016, https://run.unl.pt/bitstream/10362/19003/1/Dhadge_2016.pdf, 170 pages.
Safarik et al., "Magnetic Techniques for the Isolation and Purification of Proteins and Peptides," BioMagnetic Research and Technology, 2004, 2:7, pp. 1-17.
Thermo Scientific, Product Information Sheet, "Pierce Protein A/G Magnetic Agarose Beads," 2016, https://www.thermofisher.com/order/catalog/product/78609, 4 pages.
Warikoo et al., "Integrated Continuous Production of Recombinant Therapeutic Proteins," Biotechnology and Bioengineering, 2012, 109(12):3018-3029.
Peuker, U .A. et al. Bioseparation, magnetic particle adsorbents. Chapter 13. In: Downstream Industrial Biotechnology. Copyright 2013. John Wiley & Sons, Inc. Ed.: M.C. Flickinger. pp. 201-220; specif. pp. 203,204,206,210,216,217.
Ghose, S. Protein adsorption, expanded bed. Chapter 8. In: Downstream Industrial Biotechnology. Copyright 2013. John Wiley & Sons, Inc. Ed.: M.C. Flickinger. pp. 115-125; specif. pp. 117, 121.
Earhart, C. M. 2010. A microfabricated magnetic sifter and high throughput physical fabrication of magnetic nanoparticles for applications in protein and cell separation. PhD dissertation. Stanford Univ. pp. 1-170; specif. pp. 5, 6.
Japanese Office Action for JP Application No. 2019-535894 dated Sep. 13, 2021 (3 pages, with English translation of Abstract).
Non-Final Office Action Issued in U.S. Appl. No. 16/470,607, dated Aug. 1, 2022. (30 pages).

* cited by examiner

MAGNETIC IMMUNOGLOBULIN-BINDING PARTICLES

CROSS REFERENCE TO RELATED APPLICATIONS

This application claims the priority benefit of PCT/EP2017/084033 filed on Dec. 21, 2017 which claims priority benefit of Great Britain Application Nos. 1622307.5, 162304.2, and 1622305.9, all of which were filed Dec. 28, 2016. The entire contents of which are hereby incorporated by reference herein.

SEQUENCE LISTING

The instant application contains a Sequence Listing which has been submitted electronically in ASCII format and is hereby incorporated by reference in its entirety. Said ASCII copy, created on Jun. 5, 2019, is named 317993_ST25.txt and is 4,096 bytes in size.

REFERENCE TO CO-PENDING APPLICATION

Our application is hereby incorporated by reference in its entirety.

TECHNICAL FIELD OF THE INVENTION

The present invention relates to separation resins, and more particularly to magnetic separation resins for separation of immunoglobulins. The invention also relates to methods of separating immunoglobulins and other target biomolecules and to an apparatus for performing such methods.

BACKGROUND OF THE INVENTION

Magnetic adsorbent beads for biomolecules have been known for a long time and are commonly used for small scale lab separations of e.g. proteins, particularly for parallel separations where the magnetic format is amenable to automation by robotics. The magnetic beads are however not normally used for large scale separation of biopharmaceuticals, due to a lack of suitable beads and process designs.

Accordingly, there is a need for magnetic adsorbent beads suitable for large scale processing of biopharmaceuticals, particularly for high volume products like monoclonal antibodies. There is also a need for suitable large-scale biopharmaceutical separation processes using magnetic adsorbent beads.

SUMMARY OF THE INVENTION

One aspect of the invention is to provide a magnetic bead capable of binding immunoglobulins with a high binding strength and to a high binding capacity. This is achieved with an immunoglobulin-binding magnetic bead, comprising a porous matrix and one or more magnetic particles embedded in the matrix, where the matrix comprises a porous polymer and at least 10 mg/ml Fc-binding proteinaceous ligands covalently coupled to the porous polymer.

One advantage is that the beads allow the selective binding of large amounts of immunoglobulin directly from unclarified cell cultures having high antibody titers. A further advantage is that the beads have a favourable adsorption isotherm for immunoglobulins, giving a high yield of recovered immunoglobulin.

A second aspect of the invention is to provide an efficient method of capturing a target biomolecule from a cell culture, without previous clarification of the cell culture. This is achieved with a method of separating a target biomolecule from a cell culture, comprising the steps of:
a) providing a plurality of magnetic beads capable of binding the target biomolecule;
b) contacting the plurality of beads with a cell culture comprising a target biomolecule, to bind the target biomolecule to the beads. Step b) may be performed in a bioreactor vessel and/or the cell culture may be unclarified or cell-depleted;
c) retaining the beads with a magnetic field and washing the beads with a washing liquid;
d) eluting the beads with an eluent to desorb the target biomolecule from the beads and recovering the target biomolecule in an eluate.

A third aspect of the invention is to provide a use of the magnetic beads for separation of an immunoglobulin. This is achieved with a use as defined in the claims.

A fourth aspect of the invention is to provide an apparatus for capturing a target biomolecule from a cell culture, without previous clarification of the cell culture. This is achieved with an apparatus comprising a bioreactor fluidically connected to a contactor, wherein the contactor is fluidically connected to a high gradient magnetic field separator (HGMS).

DRAWINGS

Figure 9:
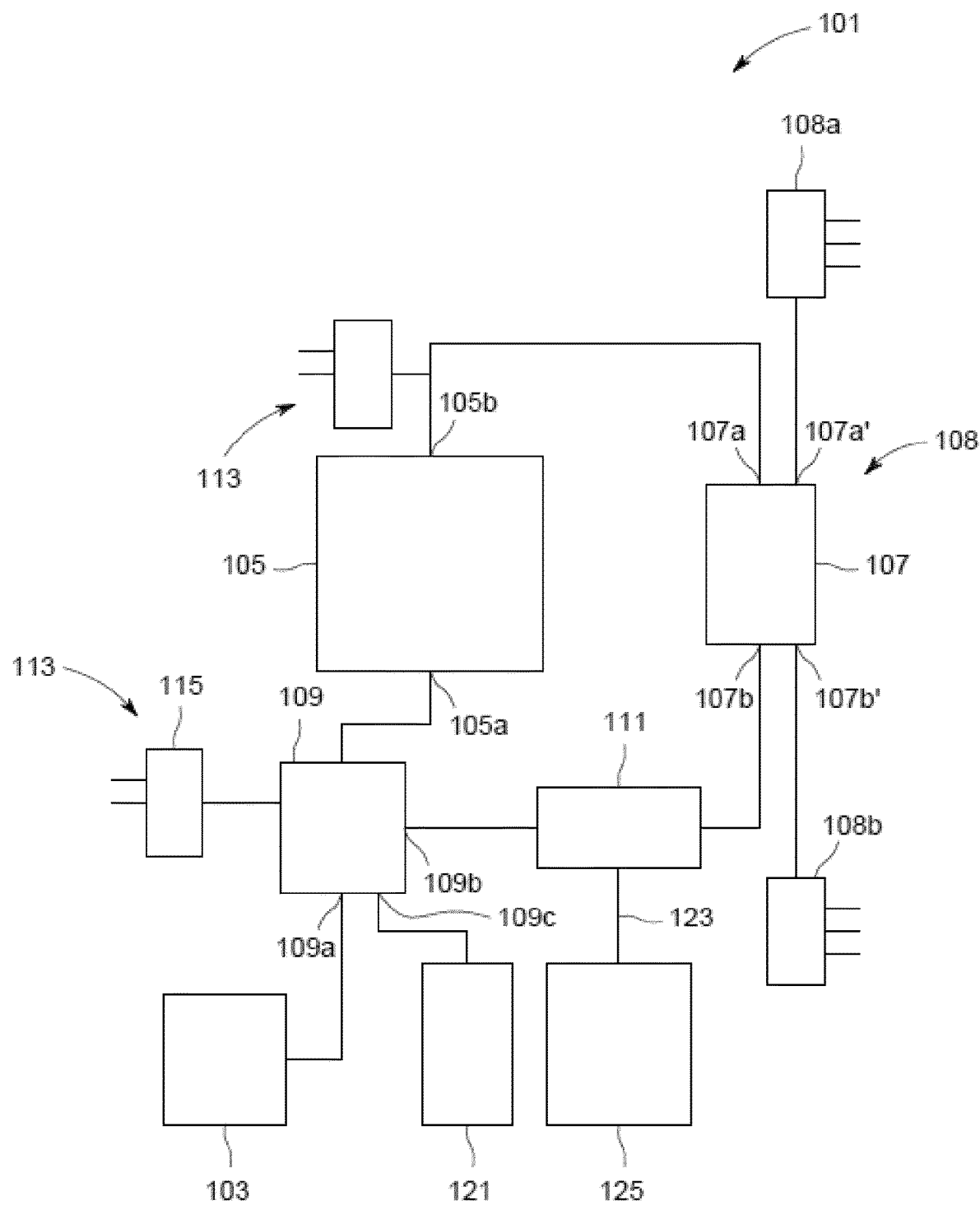

FIG. 9. shows an apparatus of the invention.

Figure 10:
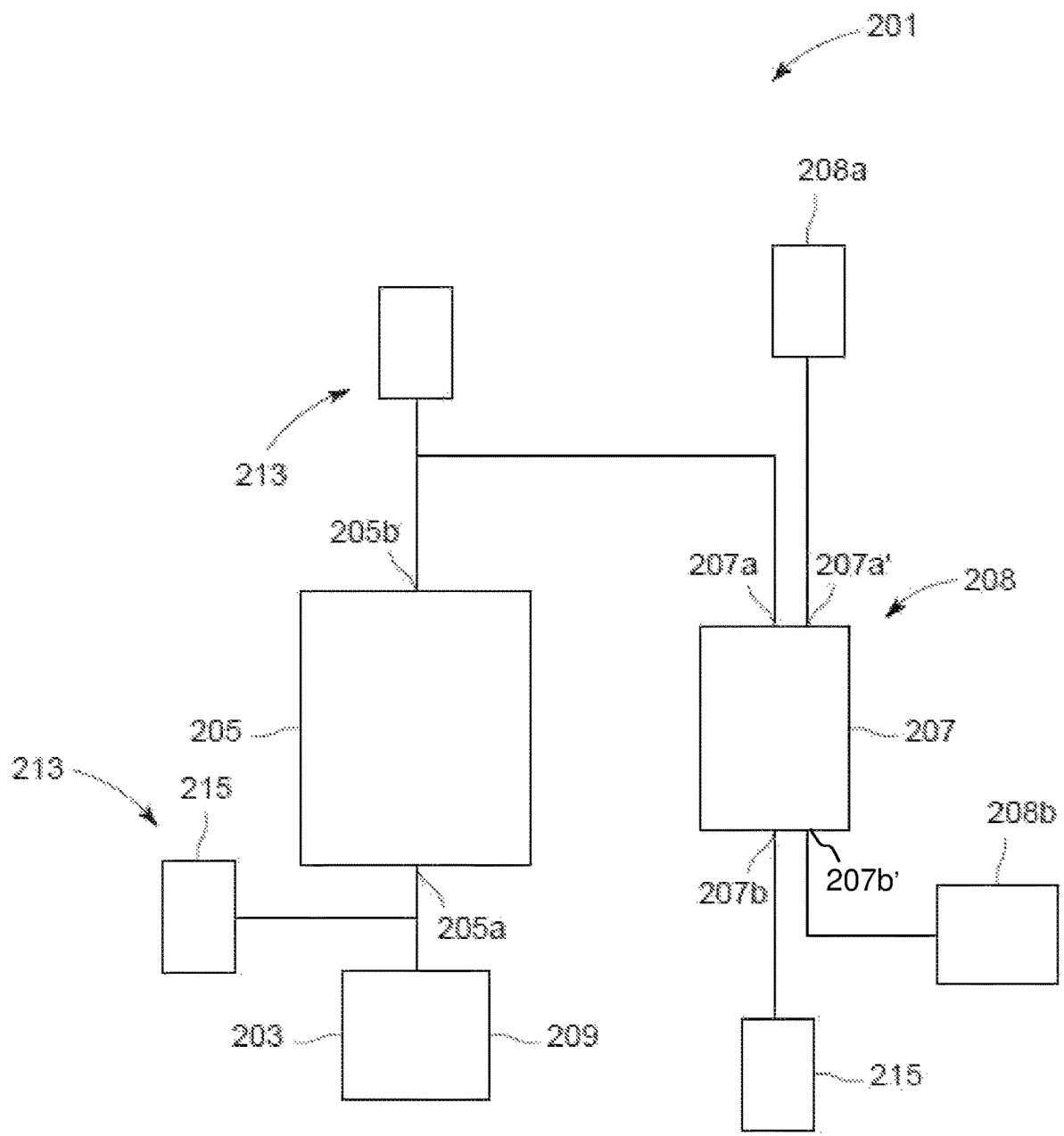

FIG. 10 shows an apparatus of the invention.

Figure 11:
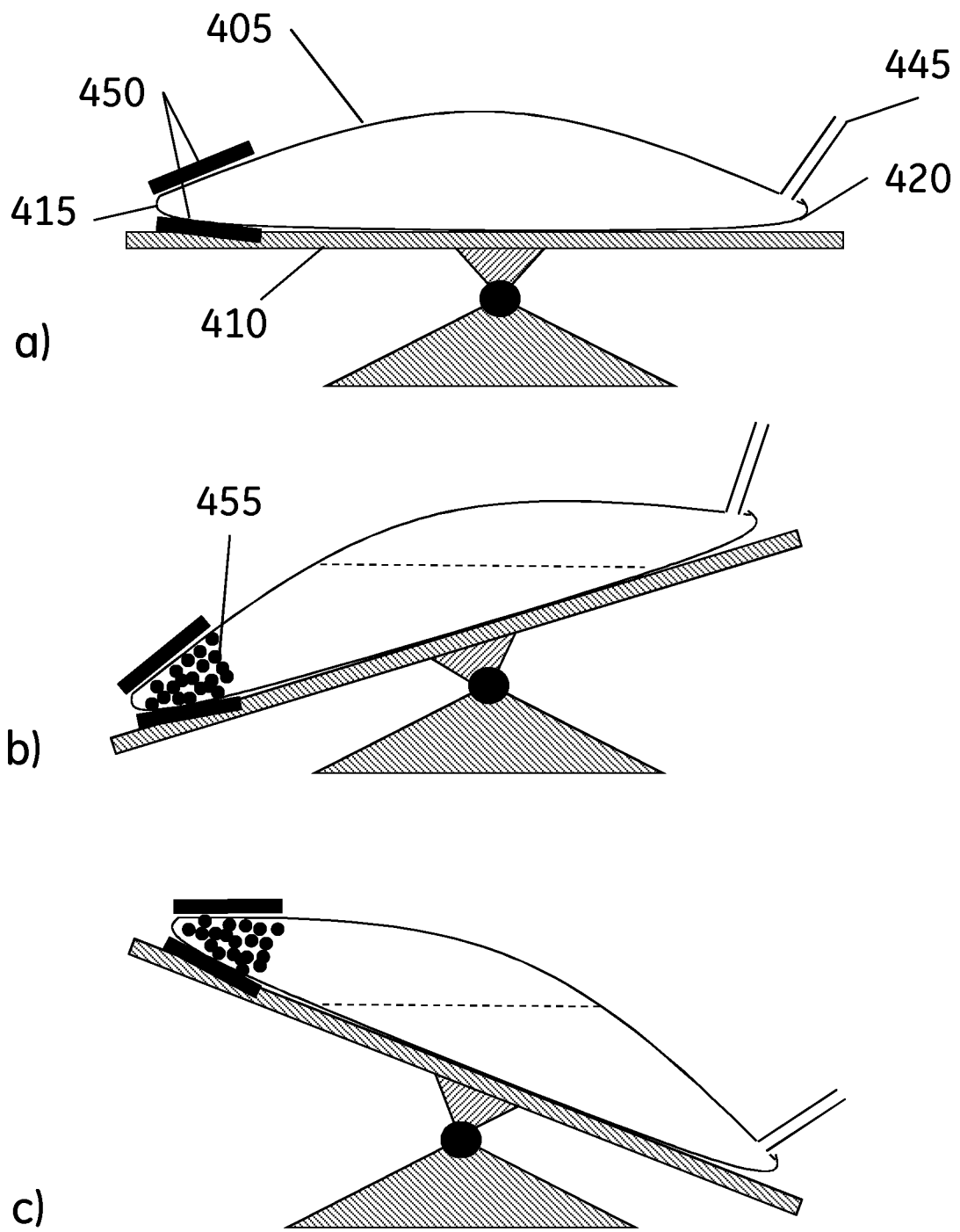

FIG. 11 shows a combined contactor/separator according to the invention.

Figure 12:
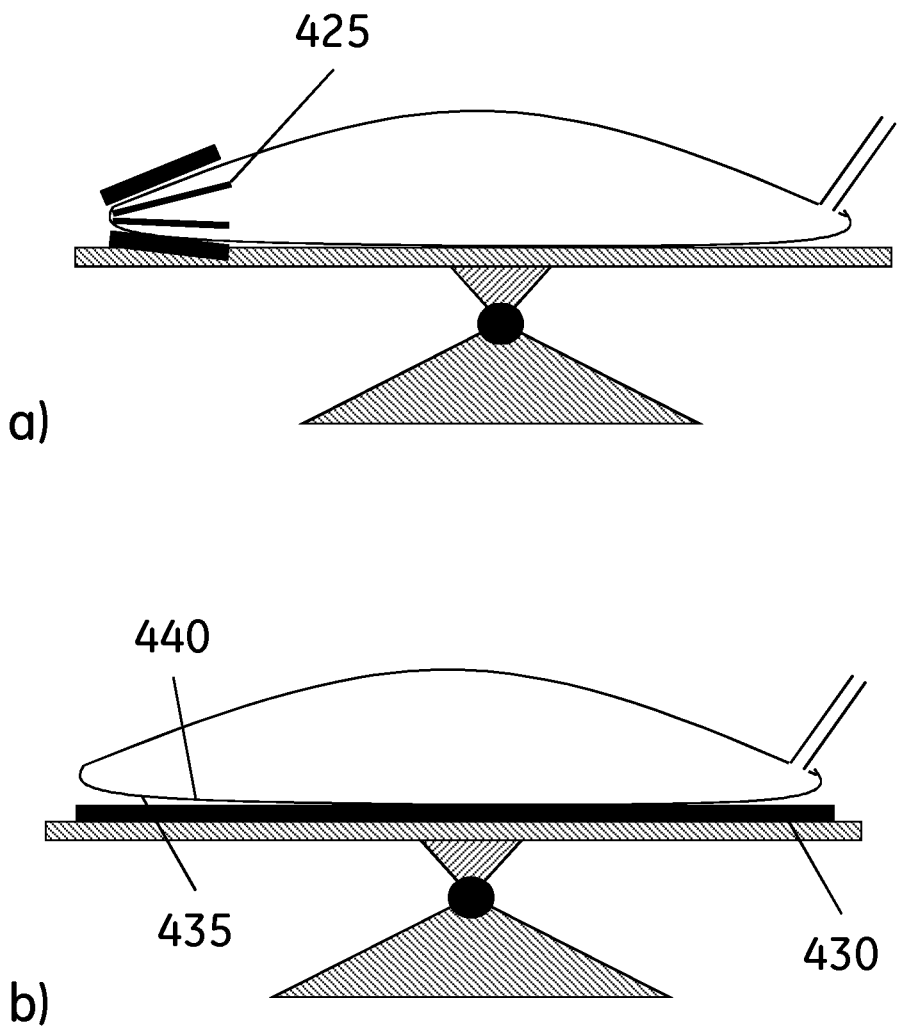

FIG. 12 shows two combined contactor/separators according to the invention.

Figure 13:
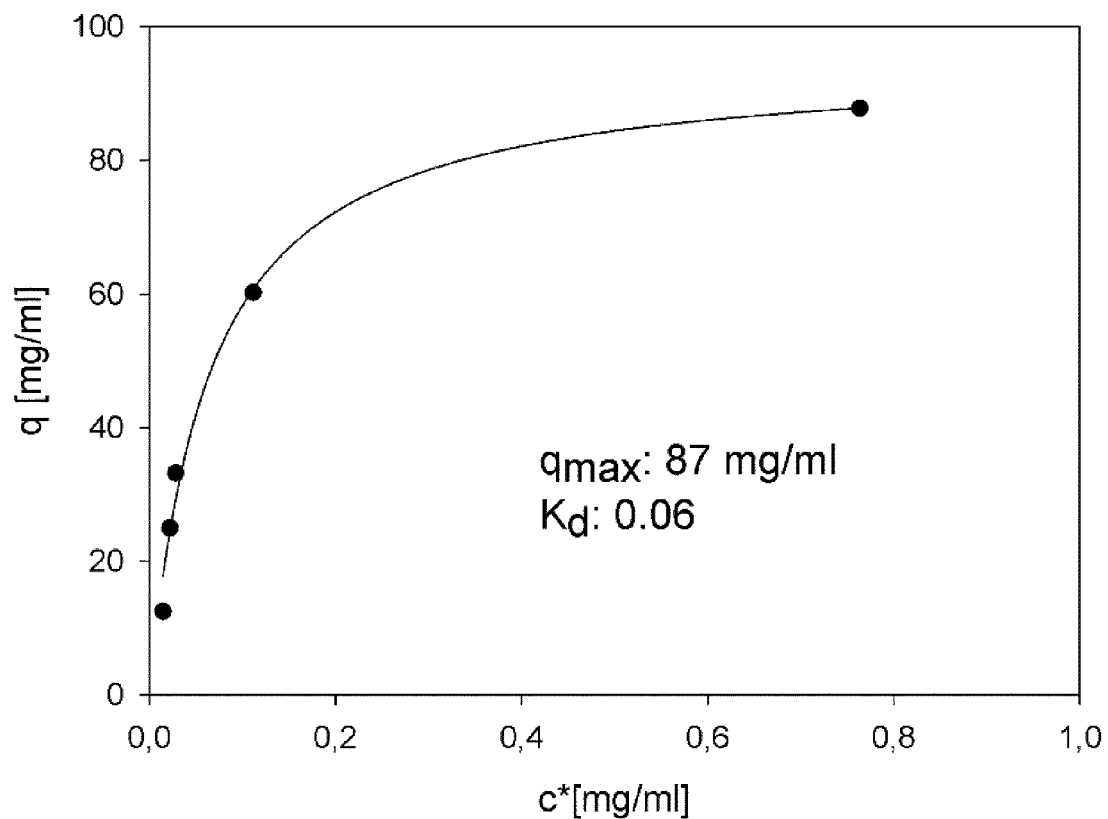

FIG. 13 shows an adsorption isotherm for an IgG monoclonal antibody on the magnetic beads of the invention.

Figure 14:
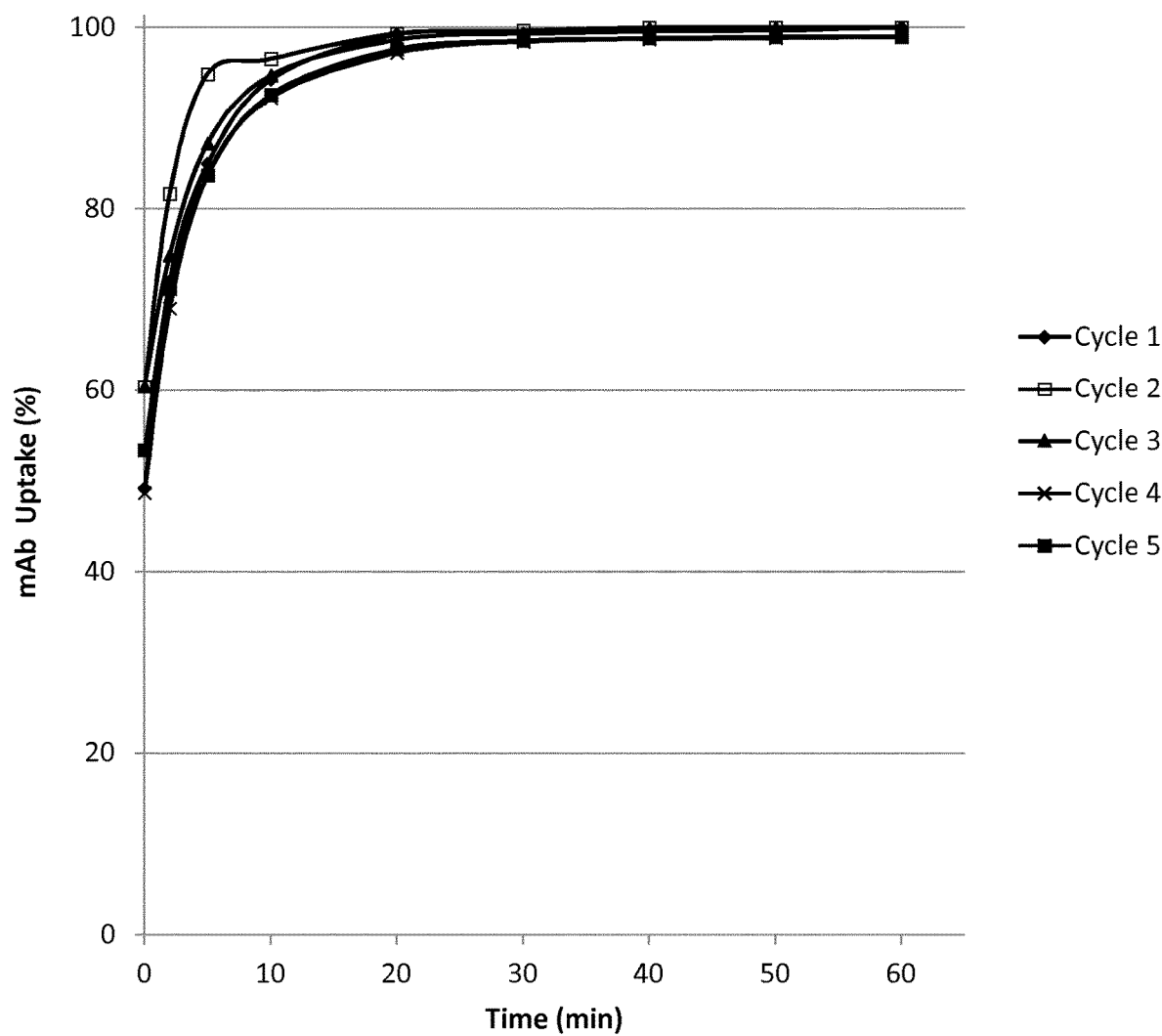

FIG. 14 shows the uptake of an IgG monoclonal antibody on the magnetic beads of the invention as a function of incubation time.

Figure 15:
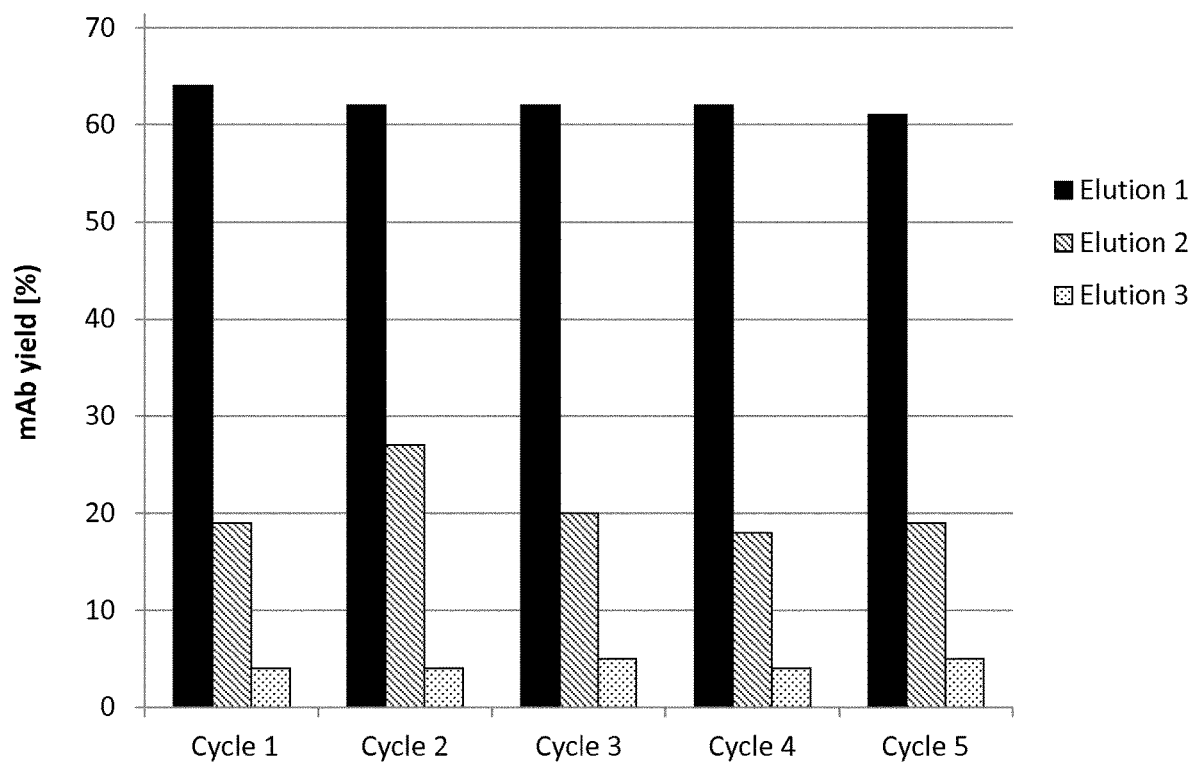

FIG. 15 shows the yield of an IgG monoclonal antibody from the magnetic beads of the invention during elution. Each elution cycle involved elution with three subsequent portions of eluent (elution 1-3).

Figure 16:
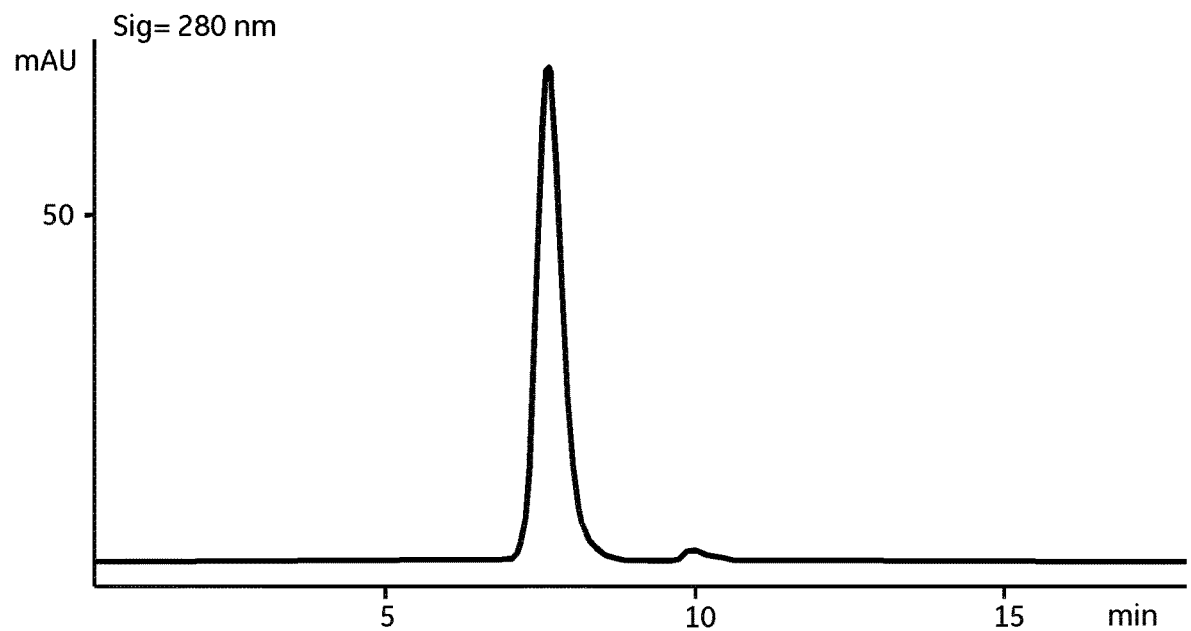
Figure 16:
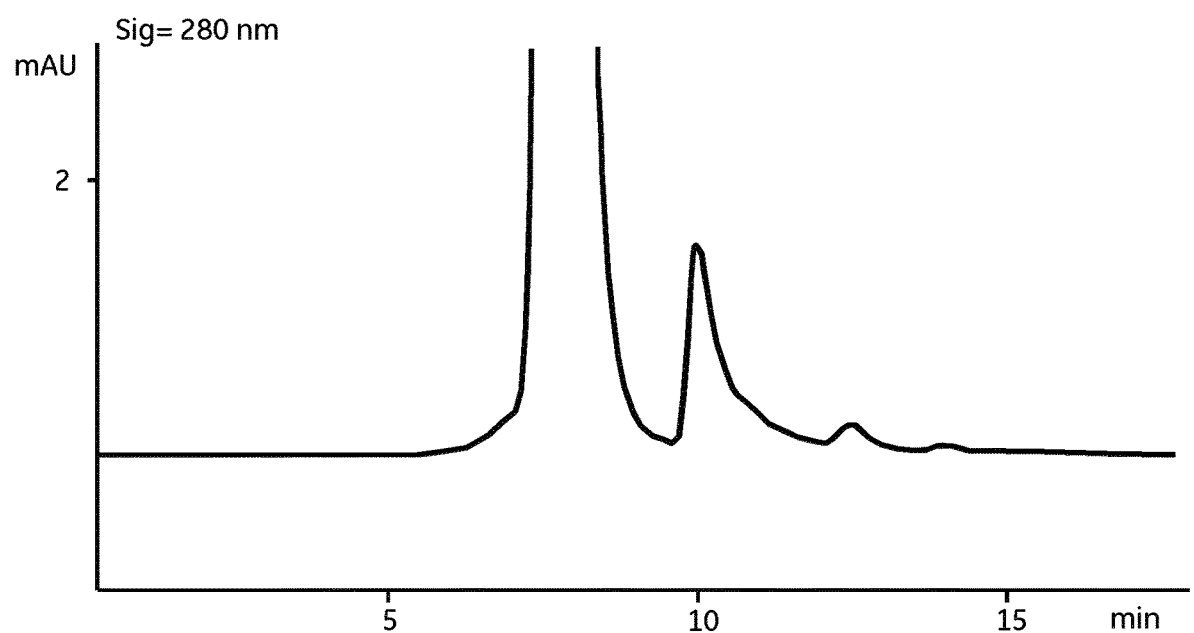

FIG. 16 shows the purity of the eluted IgG monoclonal antibody as analysed by size exclusion chromatography (SEC). a) entire chromatogram, b) magnification of the area around the main peak.

Figure 17:
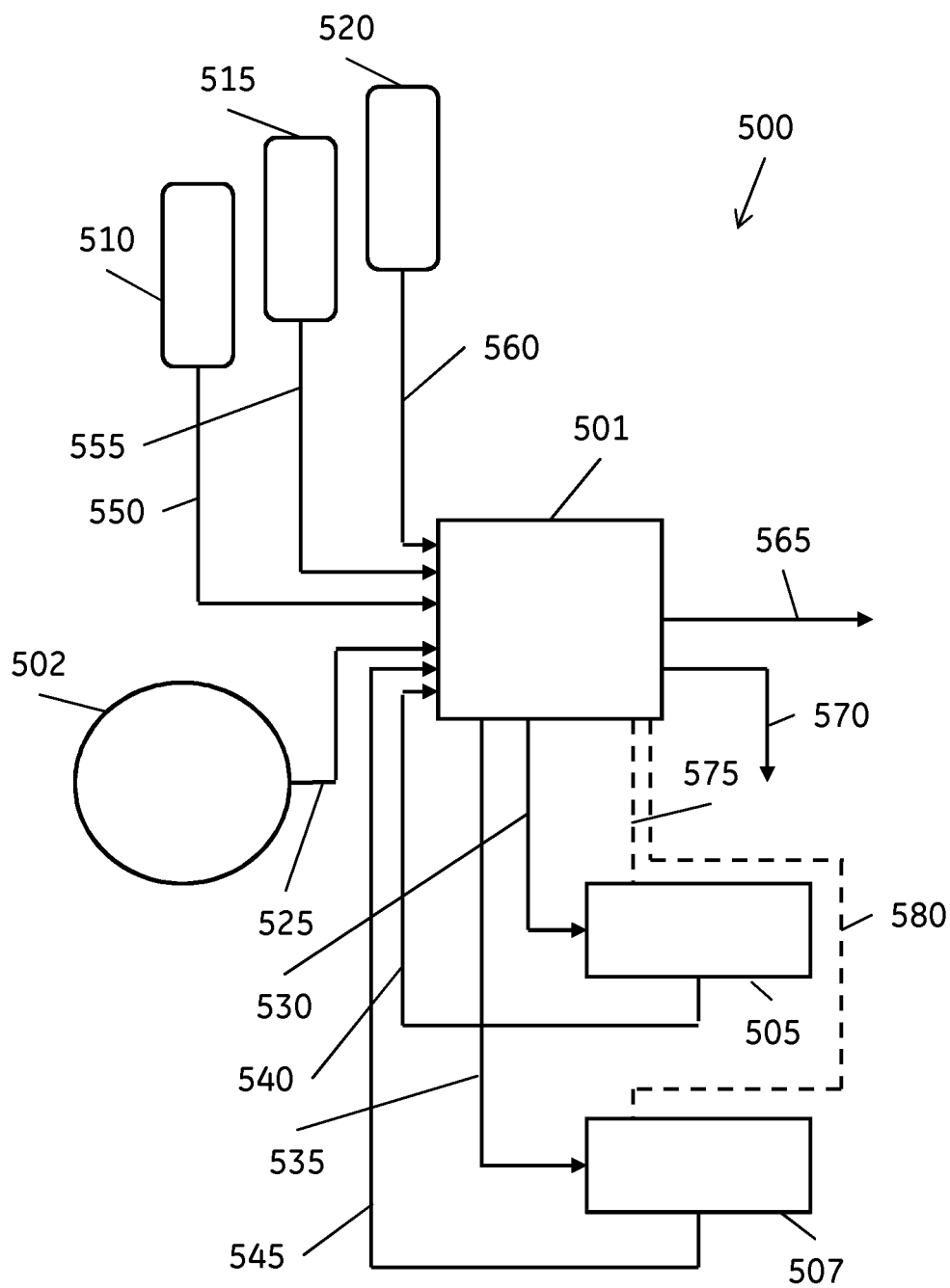

FIG. 17 shows an apparatus of the invention.

Figure 18:
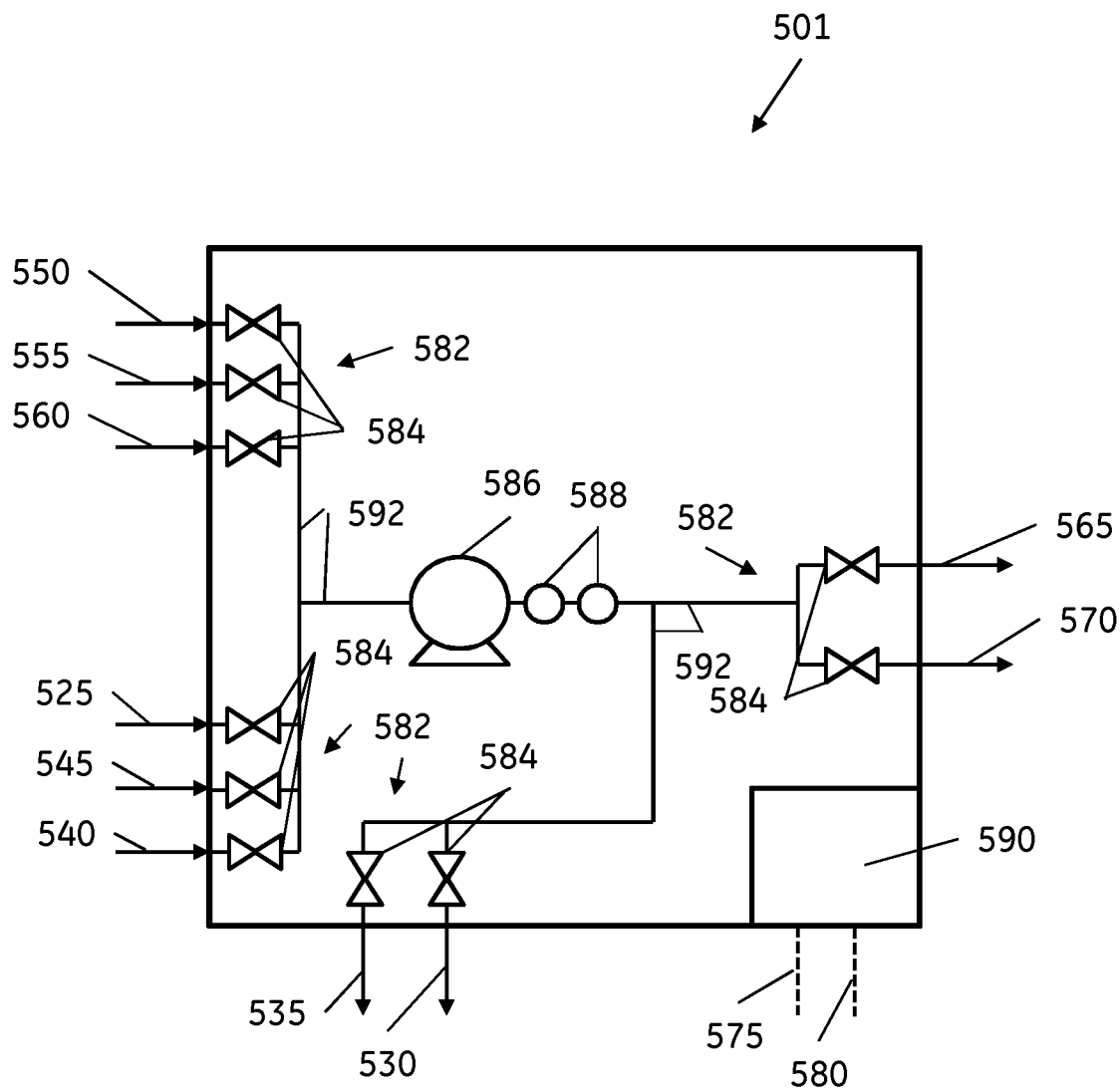

FIG. 18 shows a fluidics control system for use in the apparatus of FIG. 17.

Figure 19:
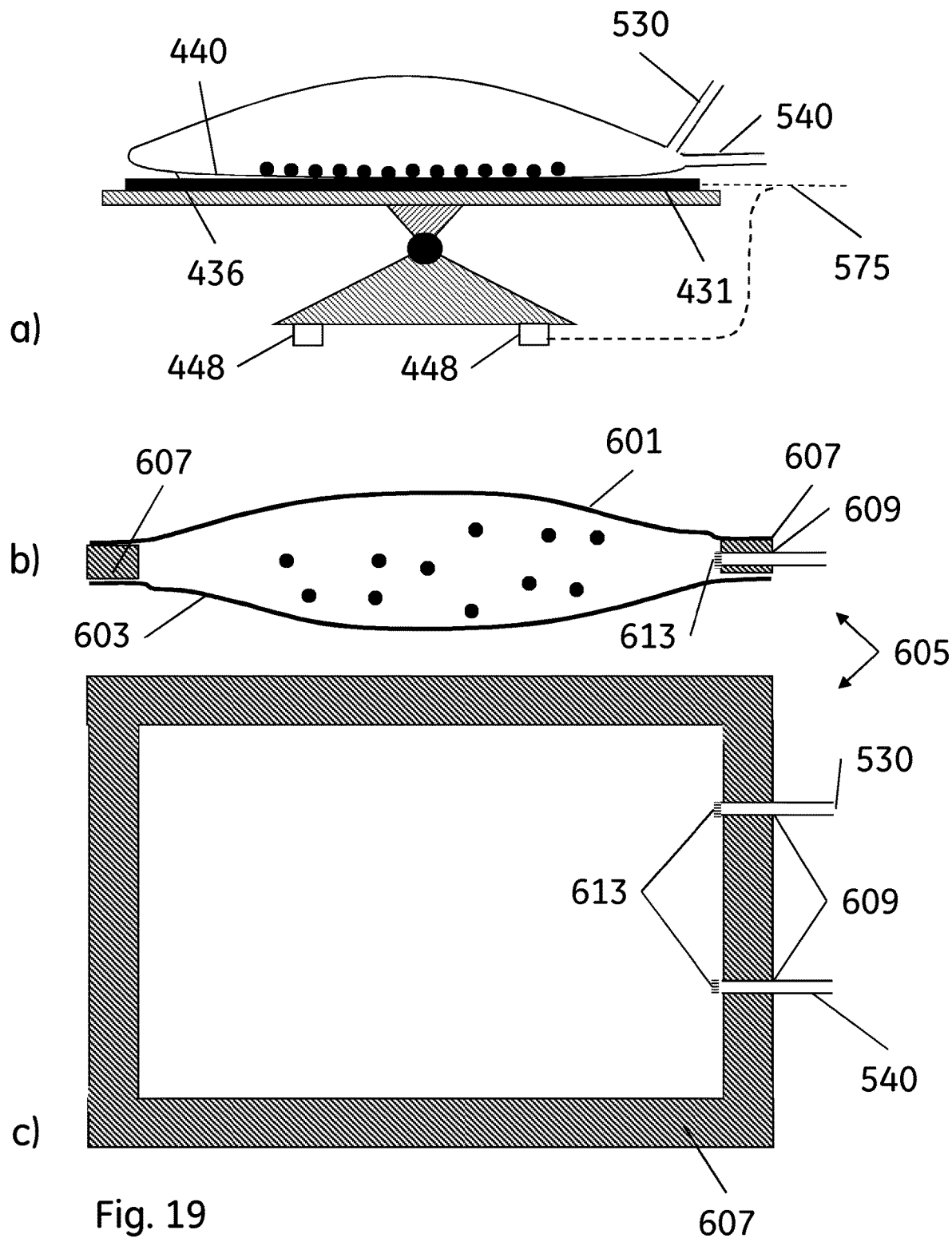

FIG. 19a) shows a combined contactor/separator according to the invention, with FIGS. 19b) and c) showing flexible bags for use in the contactor/separator.

DETAILED DESCRIPTION OF EMBODIMENTS

Figure 1:
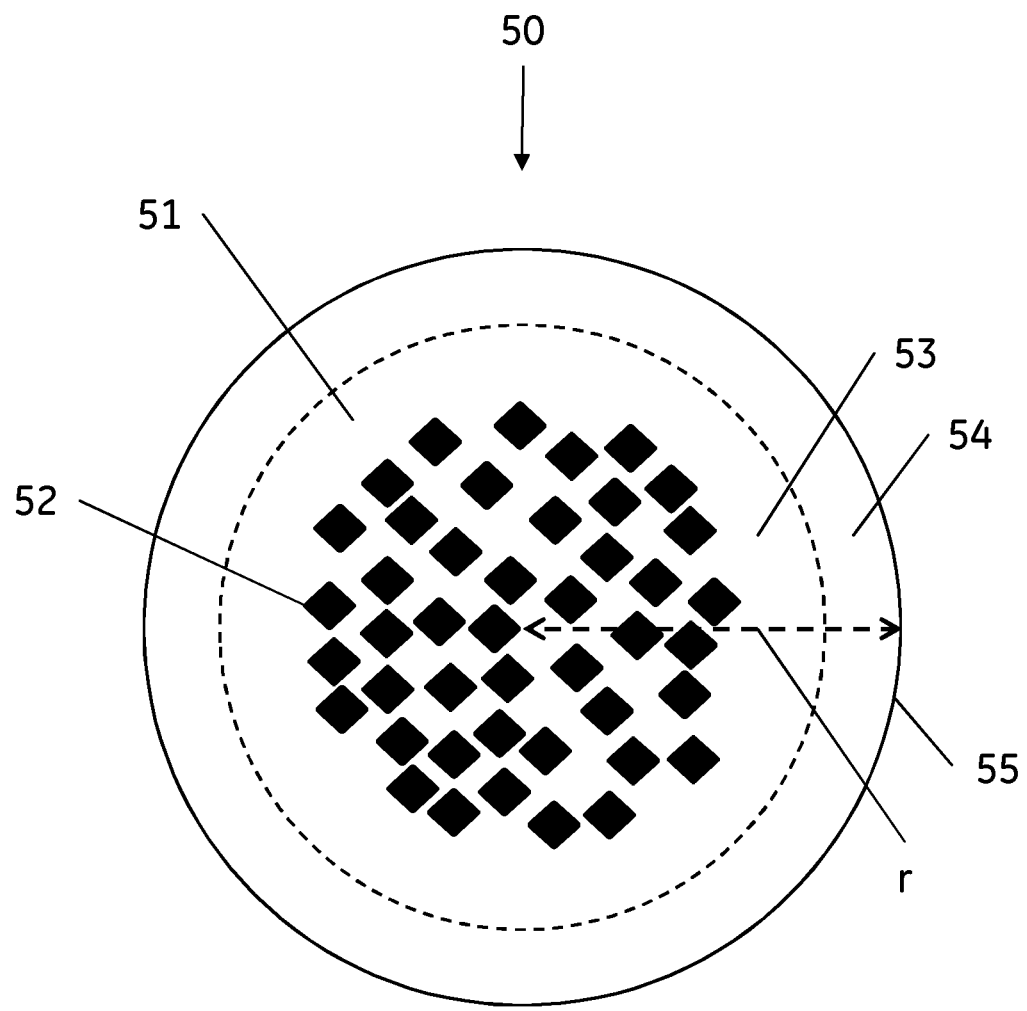
FIG. 1 shows a schematic drawing of a bead according to the invention. The drawing also shows how the magnetic particles are concentrated in a central region of the bead.

In one aspect, illustrated by FIG. 1, the present invention discloses an immunoglobulin-binding magnetic bead 50, or a plurality of such beads, comprising a porous matrix 51 and one or more magnetic particles 52 embedded in the matrix, wherein the matrix comprises a porous polymer and at least 10 mg/ml Fc-binding proteinaceous ligands covalently coupled to the porous polymer. The matrix may suitably comprise at least 15, such as at least 20 or 15-25 mg/ml, Fc-binding proteinaceous ligands covalently coupled to the porous polymer to further increase the immunoglobulin-binding capacity.

The size of the bead may suitably be such that a plurality of beads, to be used in the methods disclosed below, have a volume-weighted median diameter (d50,v) of 8-300 micrometers, such as 20-200, 20-100 micrometers or 20-80 micrometers. Beads of these sizes are easy to retain with a magnetic field, in particular compared to magnetic nanoparticles or micron-sized particles. The mass transport rates are however fast enough to give a rapid uptake of immunoglobulins by the bead. This applies in particular to beads with median diameter in the 20-100 micrometer and 20-80 micrometer intervals. The bead(s) may be spherical or essentially spherical, e.g. with a sphericity (the surface area of a sphere with the same volume as the bead divided by the surface area of the bead) of at least 0.9.

Ligands

The ligands are capable of binding to the Fc chain of immunoglobulins, i.e. the generic non-variable region of immunoglobulins (antibodies). Suitably, the ligands are capable of binding to IgG, such as the classes IgG1, IgG2 and/or IgG4. The ligands suitably have a dissociation constant $k_{off}/k_{on}$ towards IgG of 2000 pM or lower, such as 1200 pM or lower. This can be measured by immobilising the ligands on a surface plasmon resonance (SPR) chip and measuring the binding rate $k_{on}$ and the dissociation rate $k_{off}$ in an SPR instrument, e.g. Biacore (GE Healthcare). A low dissociation constant ensures that the immunoglobulin can be efficiently captured by the beads, giving a high recovery yield. The strength of the binding can also be expressed via an adsorption isotherm, measured through multiple batch uptake experiments with the beads at different immunoglobulin loadings. The amount of bound immunoglobulin is then plotted against the equilibrium immunoglobulin concentration in the solution and the data are fitted to the Langmuir equation $q=q_m c/(K+c)$, where q is the bound amount (mg/ml), c is the equilibrium solution concentration (mg/ml), K is a dissociation constant (mg/ml) and $q_m$ is the maximum binding capacity (mg/ml). A low value of K is indicative of a favourable adsorption isotherm and the beads can suitably have a value of K of less than 0.1, such as less than 0.08 for the immunoglobulin (e.g. IgG).

Suitable ligands include bacterial Fc-binders like Protein A and Protein G, as well as recombinant Fc-binders based on Fc-binding domains of these proteins. The ligands may e.g. comprise one or more Fc-binding domains of *Staphylococcus* protein A (SpA) or one or more mutants of such domains, e.g. one or more alkali-stabilized mutants of SpA Fc-binding domains. Ligands comprising such mutants are described in e.g. U.S. Pat. Nos. 8,198,404, 8,674,073, US20100221844, U.S. Pat. Nos. 9,403,883, 9,040,661, 9,051,375, 9,290,549, 8,754,196 and U.S. Ser. No. 15/282,367, which are hereby incorporated by reference in their entireties. Specifically, the ligands may comprise one or more domains as defined by the amino acid sequence SEQ ID NO:1. The ligands may comprise multimers of the domains, optionally linked by linker sequences of 1-15 amino acid residues, as in SEQ ID NO:2, a tetramer of SEQ ID NO:1, with the linker sequence VDAKFD. The ligands may further comprise a leader sequence at the N-terminus and a tailing sequence at the C-terminus. SEQ ID NO:2 has an AQGTVDAKFD leader sequence and a single cysteine (C) as the tailing sequence. The leader or tailing sequence can suitably comprise a coupling group (e.g. the thiol of a cysteine) for covalent end-point coupling of the ligand on the porous polymer (e.g. with a thioether bond when a cysteine is used for coupling).

```
                                          SEQ ID NO: 1
KEQQ NAFYEILHLP NLTEEQRNAF IQSLKDDPSQ SANLLAEAKK

LNDAQAPK

SEQ ID NO: 2
AQGT VDAKFDKEQQ NAFYEILHLP NLTEEQRNAF IQSLKDDPSQ

SANLLAEAKK LNDAQAPK VDAKFDKEQQ NAFYEILHLP

NLTEEQRNAF IQSLKDDPSQ SANLLAEAKK LNDAQAPK

VDAKFDKEQQ NAFYEILHLP NLTEEQRNAF IQSLKDDPSQ

SANLLAEAKK LNDAQAPK VDAKFDKEQQ NAFYEILHLP

NLTEEQRNAF IQSLKDDPSQ SANLLAEAKK LNDAQAPKC
```

Porous Polymer

The porous polymer may suitably be crosslinked to provide chemical and thermal stability. Suitably, the porous polymer may be a polysaccharide, which provides a high degree of hydrophilicity and low or zero non-specific adsorption. The polysaccharide may e.g. be agarose or agar, which provide highly porous gel structures through thermal gelation. These can be crosslinked e.g. by reaction with diepoxides or epichlorohydrin to generate chemically stable and hydrophilic hydroxyalkylether crosslinks. The concentration of the crosslinked polymer in the porous matrix may e.g. be 1-6 wt. %, such as 2-5 or 3-5 wt. % (as measured in the wet state). Such low concentrations provide a high porosity, allowing rapid mass transport, and since magnetic separation does not involve high back pressures as in packed bed chromatography, there is no need to provide high rigidity by increasing the concentration/solids content. The concentration of the porous polymer may be determined by a) removing any proteinaceous ligands with a protease, b) draining the beads and measuring the wet weight $w_w$, c) drying the beads and measuring the dry weight $w_d$ and c) ashing the dried beads and measuring the ash weight $w_a$. The porous polymer concentration will then be $100*(w_d-w_a)/(w_w-w_a)$. The porosity/pore size of hydrogels such as porous polysaccharides is best measured by inverse size exclusion chromatography, where a probe species is injected and the fraction of the pore volume accessible to this probe species is calculated from the retention times as the $K_{av}$ or $K_d$ value. Suitably, a $K_{av}$ value for dextran of Mw 100 kDa as the probe species, determined by inverse size exclusion chromatography on a column packed with a plurality of the beads, is 0.5-0.9, such as 0.5-0.8, 0.5-0.7 or 0.5-0.6. The determination can e.g. be made according to the methods described in Gel Filtration Principles and Methods, Pharmacia LKB Biotechnology 1991, pp 6-13. Kav is determined as the ratio $(V_e-V_0)/(V_t-V_0)$, where Ve is the elution volume of a probe molecule (e.g. Dextran 100 kD), $V_0$ is the void volume of the column (e.g. the elution volume of a high Mw void marker, such as raw dextran) and $V_t$ is the total volume of the column. $K_d$ can be determined as $(V_e-V_0)/V_i$, where $V_i$ is the elution volume of a salt (e.g. NaCl) able to access all the volume except the matrix volume (the volume occupied by the matrix polymer molecules and the magnetic particles). By definition, both $K_d$ and Kav values always lie within the range 0-1.

Magnetic Particles

The magnetic particles can suitably be ferrimagnetic, or alternatively ferromagnetic. Suitably, the magnetic particles may comprise magnetite or maghemite, which are easily available, chemically stable and have suitable ferrimagnetic properties. Magnetite can be particularly suitable. Alternatively, magnetic alloys (typically comprising iron, nickel and/or cobalt) may be used. In this case the corrosion resistance of the alloy should preferably be high enough to prevent leakage of metal ions during normal use. The bead(s) can e.g. comprise 5-15 wt. % of the magnetic particles, to make the beads sufficiently easy to retain with a magnetic field, but without increasing the density too much and avoiding obstruction of the mass transport in the porous matrix. 5-15 wt. % of a material like magnetite with density 5.2 g/ml only corresponds to 1-3 volume %. Suitably, the bead(s) may have a density (average value) of 1.05-1.20 g/ml, such as 1.07-1.15 g/ml (as measured in the wet state). The magnetic particles may e.g. have a volume-weighted median diameter (d50,v) of 1-5 micrometers. Such particles are easy to disperse in the porous matrix during manufacturing and since they are considerably smaller than the preferred bead diameter, they will not affect the shape of the beads. Advantageously, the concentration of the particles in a central region 53 of the bead is at least 200%, such as at least 400%, of the concentration in a surface region 54 of the bead. The central region is here defined as having a distance of >0.2 bead radii r from the bead surface 55 and the surface region is defined as having a distance of <0.2 bead radii from the bead surface. Having the magnetic particles concentrated in the central region is advantageous for the mass transport and facilitates the capture of the immunoglobulins by the beads. The magnetic particle distribution can be assessed by light microscopy as in FIG. 2 and for higher accuracy measurements, confocal microscopy can be used to measure the three-dimensional distribution.

Figure 3:
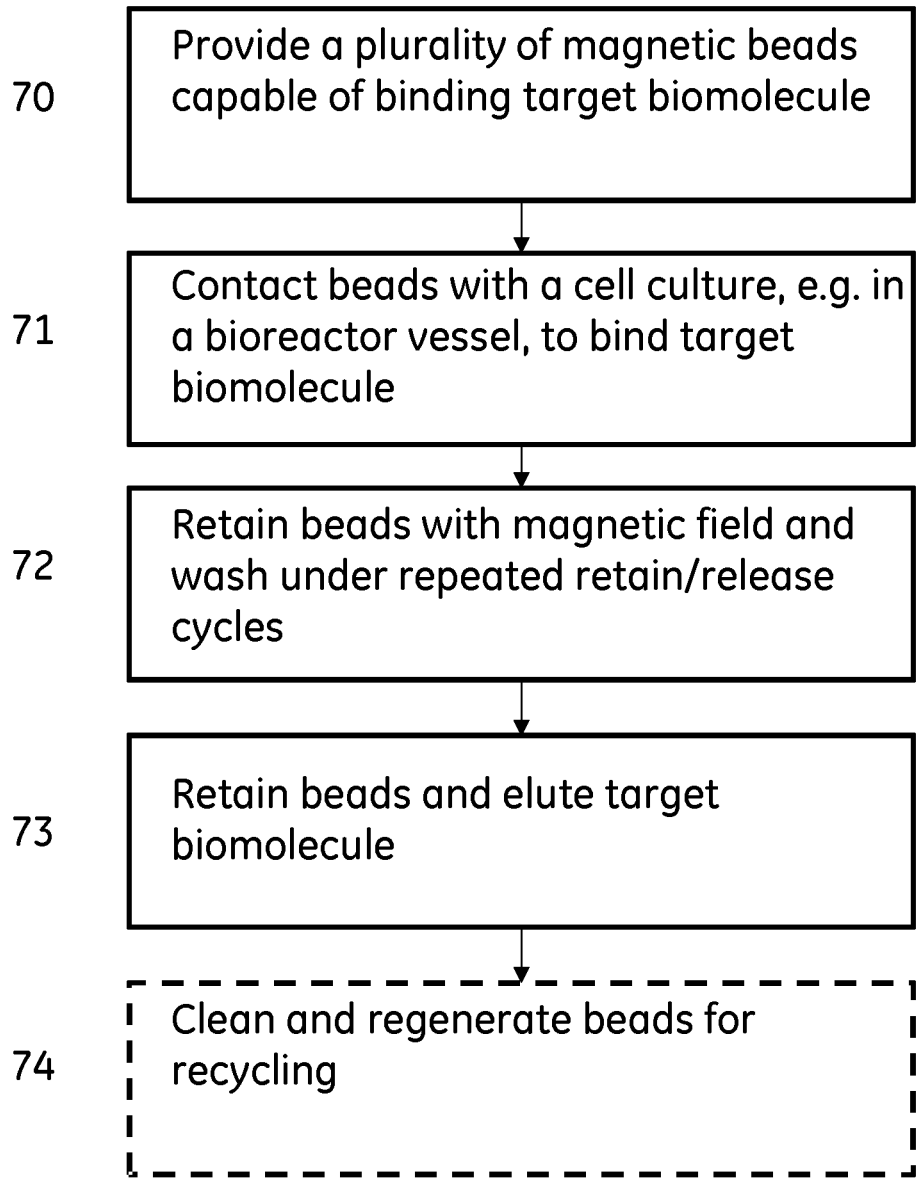
FIG. 3 shows a flow diagram of a method of the invention.

In a second aspect, illustrated by FIG. 3, the present invention discloses a method of separating a target biomolecule from a cell culture, comprising the steps of:

a) Providing a plurality of magnetic beads capable of binding the target biomolecule 70. The target biomolecule can suitably be an immunoglobulin, such as IgG, and the magnetic beads can suitably be according to any embodiments disclosed above. The magnetic beads can suitably be presterilized, e.g. by autoclaving or by radiation sterilization and they can be supplied in a presterilized bead container, suitably connected to the bioreactor vessel via presterilized tubing and one or more aseptic connections. The presterilized beads may e.g. be supplied dry in an aseptic container equipped with transfer tubing and a gas inlet. The dry beads may then be pneumatically delivered to the bioreactor vessel, e.g. as disclosed in WO2016188781 (U.S. application Ser. No. 15/573,960), which is hereby incorporated by reference in its entirety. Dry beads can be re-swollen either in a buffer or directly in the cell culture. Alternatively, the presterilized beads may be contained in a pouch inside the bioreactor vessel, which can be opened by action from the outside, e.g. by rupturing a weak seam in the pouch, to bring the beads into contact with the cell culture;

b) Contacting the plurality of beads with an unclarified or cell-depleted cell culture comprising a target biomolecule, to bind the target biomolecule to the beads 71. The cell culture can be unclarified, e.g. taken directly from a bioreactor without any subsequent cell/particle removal steps. Alternatively, it can be cell-depleted, e.g. where a fraction (but not all) of the particulates such as cells and/or cell debris have been removed. The turbidity of a cell-depleted cell culture can e.g. be at least 100 NTU, such as at least 200 or at least 500 NTU, while the turbidity of a cell culture before any removal of particulates may be at least 1000 NTU, such as at least 2000 NTU or even completely opaque. In certain embodiments the beads are added directly to the cell culture in a bioreactor vessel where the cells have been cultivated or are undergoing cultivation. Performing the cultivation in the presence of the beads can be particularly advantageous if the expression is down-regulated or otherwise negatively affected by the target biomolecule, so that the concentration of free target biomolecule is kept low in the culture. The unclarified or cell-depleted cell culture may e.g. comprise at least 1 mg/ml target biomolecule or immunoglobulin, such as at least 2 or at least 2.5 mg/ml target biomolecule or immunoglobulin. The amount of magnetic beads contacted with the unclarified or cell-depleted cell culture may be optimized depending on the concentration of the target biomolecule/immunoglobulin and the binding capacity of the beads. Typically, 50-200 ml beads per liter cell culture may be contacted with the unclarified or cell-depleted cell culture. The beads may be unused beads or they may be recirculated, e.g. from step d) as described below. The contacting of the beads with the cell culture may be performed directly in a bioreactor or e.g. in a contactor. A contactor may be a vessel to which the cell culture and the beads are conveyed and which may be agitated to some extent to provide rapid mass transport into the beads. The bioreactor vessel or the contactor may e.g. be a flexible bag, such as a flexible plastic bag with one or more inlet and outlet ports. Such a bag can be agitated in several ways, one of which is to place the bag on a rocking tray as disclosed e.g. in U.S. Pat. Nos. 6,190,913, 7,195,394 and US20130316446, which are hereby incorporated by reference in their entireties. The tray can typically be adapted to rock back and forth around a horizontal axis located below the tray and the rocking motion may be actuated by e.g. an electric motor and/or one or more pneumatic cylinders. The use of a rocking tray for agitation means that no moving agitators need to be placed in the vessel. This means that neither shaft seals nor magnetically driven impellers are needed. Shaft seals are sensitive constructions from a sterility point of view and magnetically driven impellers may interact with the magnetic beads in undesirable ways. The tray can further be arranged to pivot into an upright position, as disclosed in US20130316446, around a second horizontal axis. This allows for convenient draining and transport of the beads and cell culture out of the bag into further units for carrying out steps c) and d). The pivoting may be manual as indicated in US20130316446, but it may also be automated, driven e.g. by one or more linear drives or hydraulic cylinders.

c) Retaining the beads with a magnetic field and washing the beads with a washing liquid 72. This step may e.g. comprise a sequence of:

i) removing the magnetic field;
ii) resuspending the beads;
iii) contacting the beads with a portion of washing liquid;
iv) retaining the beads with a magnetic field; and
v) removing washing liquid from the retained beads.

Step c) may be carried out in a high gradient magnetic field separator (HGMS). HGMS are known in the art, see e.g. U.S. Pat. Nos. 7,506,765, 6,180,005, US20120132593, U.S. Pat. Nos. 6,688,473 and 7,223,345, which are hereby incorporated by reference in their entireties. They typically comprise a separation chamber with an inlet and an outlet and magnetizable elements, e.g. disks, wires or tubes, inside the chamber. When a magnetic field is applied over the chamber, e.g. with an electromagnet, the field is amplified by the magnetizable elements and any magnetic particles are retained on the elements. When the magnetic field is removed, the retained magnetic particles will be released from the elements and can be redispersed, optionally assisted by movable elements/agitators inside the separation chamber. In a typical sequence of step c), the magnetic beads with the cell culture are conveyed (e.g. pumped, entrained by a liquid stream or fed by gravity) from the contactor or bioreactor of step b) into the separation chamber of a HGMS and the magnetic field is applied to retain the beads while the cell culture is drained from the chamber. Then, substeps i)-v) as disclosed above are applied to perform a washing operation. For improved washing efficiency, substeps i)-v) can then be repeated one or more times. The repeated resuspending of the beads means that any particulates (cells and/or cell debris) entangled with or adhering to the beads will be efficiently removed. The washing liquid may be an aqueous buffer and can be selected such that the target biomolecule/immunoglobulin remains strongly bound to the ligands, while impurities, contaminants and particulates are easily washed off. For the case of an immunoglobulin as the target biomolecule and Protein A-derived ligands, the washing liquid may e.g. have a pH of 5-8. The washing liquid may optionally comprise an additive for improving the washing efficiency, e.g. to improve the host cell protein clearance. Such additives are known in the Protein A packed bed chromatography art and may comprise one or more of a detergent, a water-miscible organic solvent, a chaotrope, arginine or an arginine derivative, calcium ions and tetraalkylammonium ions. The following documents describing suitable additives are hereby incorporated by reference in their entireties: U.S. Pat. Nos. 6,127,526, 6,870,034, 7,820,799, U.S. Pat. Nos. 7,834,162, 8,263,750, 7,714,111, 9,284,347, US20120283416, US20130197197, WO2014186350, WO2014192877, US20140094593, US20160108084 and US20160024147.

In alternative embodiments, steps b) and c) are carried out in a combined bioreactor vessel/contactor and magnetic separator. This can suitably be an agitated vessel to provide rapid mass transport into the beads. It can also be an agitated vessel to which the cell culture and the beads are conveyed. The vessel may e.g. be a flexible bag, such as a flexible plastic bag, suitably with one or more inlet and outlet ports. Such a bag can be agitated in several ways, one of which is to place the bag on a rocking tray as discussed above under step b) and further illustrated in FIGS. 11 and 12. To function as a magnetic separator, a magnetic field may be applied to the vessel/bag in such a way that the magnetic beads are retained by the magnetic field and the non-bound components of the cell culture can be washed away. The magnetic field can be applied simply by placing a permanent magnet or an electromagnet close to a desired part of the vessel/bag, but it may be advantageous to design the vessel/bag such that a particularly high degree of retention and an efficient washing is achieved. One example of such an arrangement is shown in FIG. 11, with a flexible bag 405 on a rocking platform 410, where a magnetic field from one or more magnets 450 is applied over a first end portion 415 of the flexible bag to retain the beads in that end portion. If the field is applied when the first end portion is in a low position of the rocking cycle, the beads 455 will be attracted by the magnetic field and retained. The bag can then be tilted until the first end portion is in a high position and the cell culture can be drained from a port 445 adjacent an opposite second end portion 420, which is now in a low position. Washing liquid can then be added, the magnetic field released (by removing permanent magnet(s) or by switching of electromagnet(s)) and the bag agitated by rocking and then the beads can be retained and the washing liquid drained in the same way as the cell culture. In this way, the same washing sequence i)-v) as discussed above under step c) can be achieved and repeated as many times as needed. If a high gradient magnetic field is needed for complete retention of the magnetic beads, this can be achieved e.g. by inserting magnetizable elements 425 in the first end portion of the bag as shown in FIG. 12a). These elements may e.g. be thin plates of a magnetic stainless steel quality. Alternatively, one or more magnets 430 could be placed in contact with a bottom surface 435 of the bag to retain the magnetic beads in a thin layer over the entire bottom 440 of the bag (FIG. 12b)). This has the advantage of decreasing the entrapment of particulates among the magnetic beads during washing and it also facilitates redispersion of the beads. The magnet(s) 430 may e.g. be one or more electromagnets that can be switched on to retain the magnetic beads and switched off to release the beads;

d) Eluting the beads with an eluent to desorb the target biomolecule from the beads and recovering the target biomolecule in an eluate 73. In this step, the beads can suitably be retained with a magnetic field, e.g. using a HGMS as described above or by using the combined bioreactor vessel and magnetic separator discussed above, but they can also be retained by other means, e.g. a net or a porous frit, as the particulates will be removed in step c) and a packed bed elution is now possible. If a HGMS is used for step d) this can be the same HGMS as used for step c), but it can also be a second HGMS to which the beads are conveyed after step c). The latter arrangement allows for optimization of the HDMS designs, such that step c) can be made in a specific washer HGMS and step d) in a specific elution HGMS. A washer HGMS needs to be designed for efficient removal of particulates, while this is not needed in an elution HGMS. For the elution HGMS it will be more important to retain the beads in a low volume, such that the target biomolecule/immunoglobulin can be recovered in as low an eluate volume as possible. A further advantage of having separate washer and elution HGMS is that it is possible to simultaneously wash and elute two separate portions of beads in a continuous recovery process. In such a process, a first bead portion is incubated with a first cell culture portion in the contactor, conveyed to the washer HGMS and washed while a second cell culture portion is incubated with a second bead portion. Next, the first bead portion is eluted in the elution HGMS, while the second bead portion is washed in the washer HGMS and a third bead portion is incubated with a third cell culture portion in the contactor. After completion of step d), the beads can either be discarded, or preferably, recirculated. In this case, they are suitably cleaned, e.g. with an alkaline cleaning agent such as 0.1 M NaOH commonly used for cleaning in place (CIP) of alkali stable Protein A media in packed bed chromatography, and then reequilibrated with an aqueous buffer suitable for contacting the cell culture 74. Typically, this can be a buffer with near-physiological pH and conductivity, such as a PBS (phosphate buffer saline) buffer. The cleaning and reequilibration may be performed in the elution HGMS but could also be performed in a separate regeneration HGMS or other retaining device if this is desirable for the timing of a continuous recovery process. After the cleaning and reequilibration, the beads may be conveyed (e.g. pumped, entrained by a liquid stream or fed by gravity) to the bioreactor vessel for reuse. They may also undergo a sterilization step before reuse, if needed. This can e.g. be done by autoclaving.

If steps b) and c) are carried out in a combined contactor and magnetic separator as disclosed above, it is also possible to carry out step d) in the same combined device.

As the particulates from the cell culture are efficiently removed in the recovery process, the eluate obtained can be directly applied to e.g. a subsequent chromatography column (e.g. an ion exchange or multimodal column for polishing) without any further clarification in filters etc. Examples of ion exchange resins for subsequent polishing includes Capto™ and Capto™ S ImpAct (GE Healthcare) and examples of multimodal resins include Capto™ adhere and Capto™ MMC (GE Healthcare). The eluate can also be directly applied to a virus removal filter without pretreatment or it can be applied to a chemical virus inactivation step.

In situations where the volume of the bioreactor is higher than the contactor/separator volume, the process may be cycled, with steps b), c) and d) repeated with several aliquots of said cell culture, e.g. 5-20 aliquots, such as 5-10 aliquots. As discussed further below, it can also be advantageous to have a plurality of contactors or combined contactors-magnetic separators, allowing parallel processing of several aliquots. Typically, one of steps b), c) and d) can be performed in one contactor or contactor-magnetic separator simultaneously with another of steps b), c) and d) in another contactor or contactor-magnetic separator. If the binding isotherm for the target biomolecule to the magnetic beads is shallow, there may also be a need for transferring the cell culture after step b) to a second contactor or combined contactor-magnetic separator for recovery of non-bound target biomolecule. This can also be conveniently handled in an apparatus with several individually addressable contactors or combined contactors-magnetic separators.

It is also possible to use magnetic beads for recovery of the target biomolecule/immunoglobulin in a continuous perfusion cultivation process. One way of doing this is to convey a stream of cell culture from a bioreactor to a cell separation device for at least partial recovery of cells and recycling the cells back to the bioreactor and replenishing the bioreactor with fresh culture medium. The cell separation device will separate the cell culture into a cell stream for recycling and a cell-depleted cell culture, which can be subjected to a recovery process with the magnetic beads as described above. As the magnetic bead recovery process is highly suitable for handle particulate-containing, turbid feeds, it is possible to use cell separation devices that do not provide a complete clarification. Examples of such separation devices include inclined settlers, as disclosed e.g. in U.S. Pat. No. 5,817,505 (hereby incorporated by reference in its entirety) and acoustic separation devices, as disclosed e.g. in U.S. Pat. Nos. 9,512,395, 9,458,450, 9,422,328 and 5,626,767 (hereby incorporated by reference in their entireties). Such devices are convenient for handling cell cultures with high cell concentrations without clogging issues, but they do not provide a complete removal of particulates, meaning that recovery of the target biomolecule/immunoglobulin using magnetic beads, where complete clarification is not needed, is very attractive.

Another alternative is to use magnetic beads for recovery of the target biomolecule/immunoglobulin in a chemostat cultivation process. Here, part of the cell culture in a bioreactor is continuously bled off and replaced with fresh culture medium so that the cultivation conditions are kept constant. The culture bleed can conveniently be collected in a contactor and the target biomolecule or immunoglobulin separated with magnetic beads as discussed in the methods above.

In combination with the above methods it is also possible to add further adsorbents or precipitants to the cell culture, e.g. for binding of undesirable contaminants. Such adsorbents/precipitants can suitably be non-magnetic, so that they or the precipitates formed can be discarded with the remaining cell culture during step b). Examples of such adsorbents include the addition of allantoin or uric acid to remove endotoxins and viruses (US20150184132, hereby incorporated by reference in its entirety) and the addition of mixed charged particles to remove aggregates from antibodies (US20150183879, hereby incorporated by reference in its entirety), while an example of a precipitant is the addition of C7-C10 fatty acids for removal of chromatin etc. (US20160009762 and US20160115194, hereby incorporated by reference in their entireties). The adsorbents or precipitates may be added either before or during step b).

In a third aspect, the present invention discloses the use of a plurality of beads as discussed above for separation of an immunoglobulin from an unclarified or cell-depleted cell culture. The use may be as described in any of the methods discussed above and the purpose of the use may be to provide an immunoglobulin of at least 90%, such as at least 95%, purity directly from an unclarified or cell-depleted cell culture. The unclarified or cell-depleted cell culture may in this context have a turbidity of at least 100 NTU, such as at least 200 or at least 500 NTU.

In a fourth aspect, the present invention discloses an apparatus (which may alternatively be called a system) comprising a bioreactor fluidically connected to a contactor, wherein the contactor is fluidically connected to a high gradient magnetic field separator (HGMS). The contactor and the HGMS may be as described above. The contactor may also be fluidically connected to a washer HGMS and said washer HGMS is fluidically connected to an elution HGMS, both as described above. Further, the bioreactor may be fluidically connected to the contactor via a cell separation device configured to deliver a cell-depleted cell culture to the contactor and to deliver recycled cells back to the bioreactor. The cell separation device may be as described above.

Figure 4:
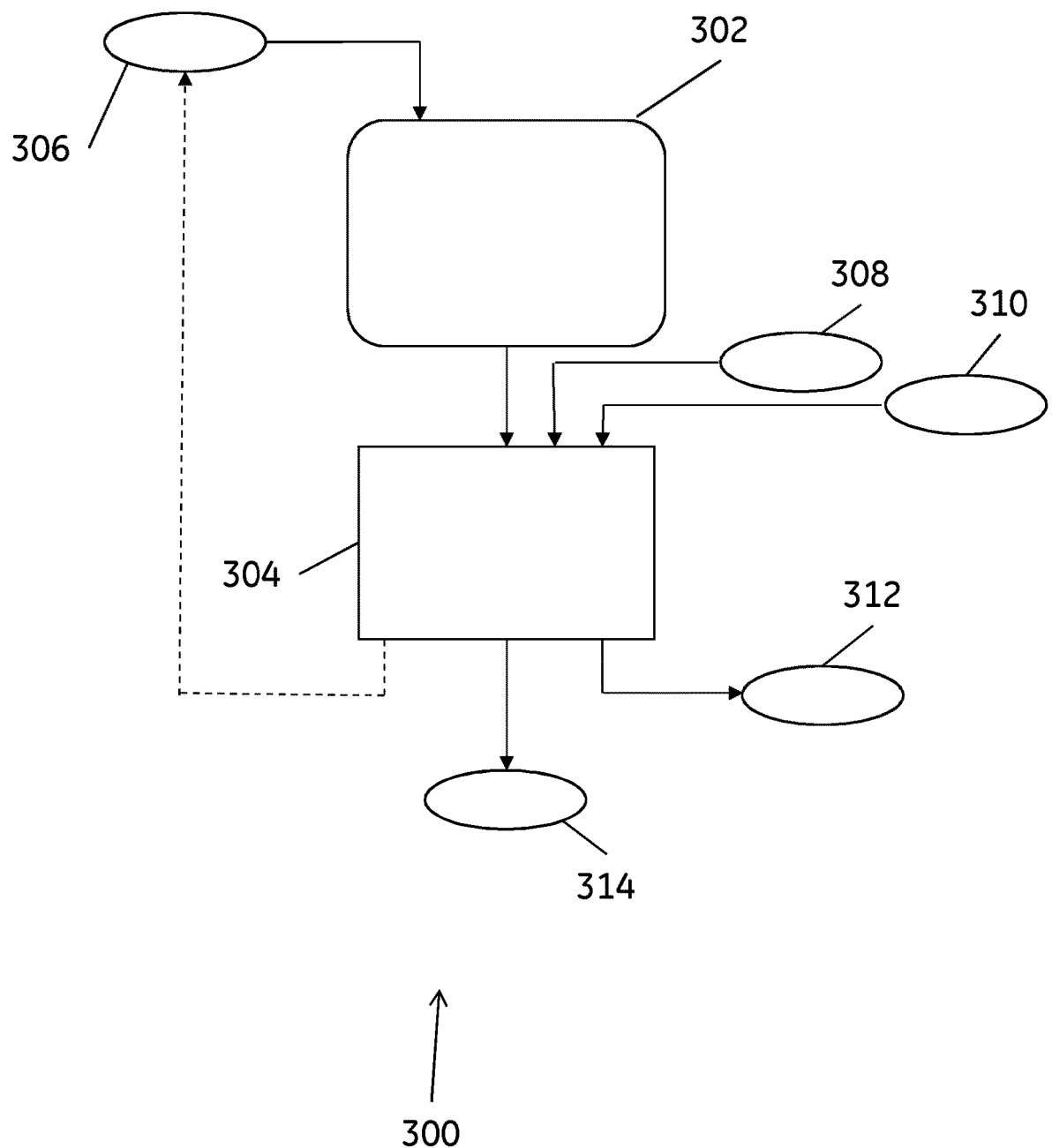
FIG. 4 shows an apparatus of the invention.

Different embodiments of the apparatus are illustrated in FIGS. 4-10:

FIG. 4. shows an apparatus 300, comprising a bioreactor 302 and a magnetic separator 304, where magnetic beads 306 can be added to the bioreactor for incubation with a cell culture (step b)). The cell culture with the beads can then be conveyed to the magnetic separator 304 for performing steps c) and d) of the method. During step c), wash liquid 308 is conveyed to the separator and during step d), eluent 310 is conveyed to the separator. An eluate 312 is recovered during step d) and spent cell culture and wash liquid is conveyed to a waste outlet 314 during step c). If the beads are cleaned and regenerated during step d), they can optionally be recycled to the bioreactor (not shown).

Figure 5:
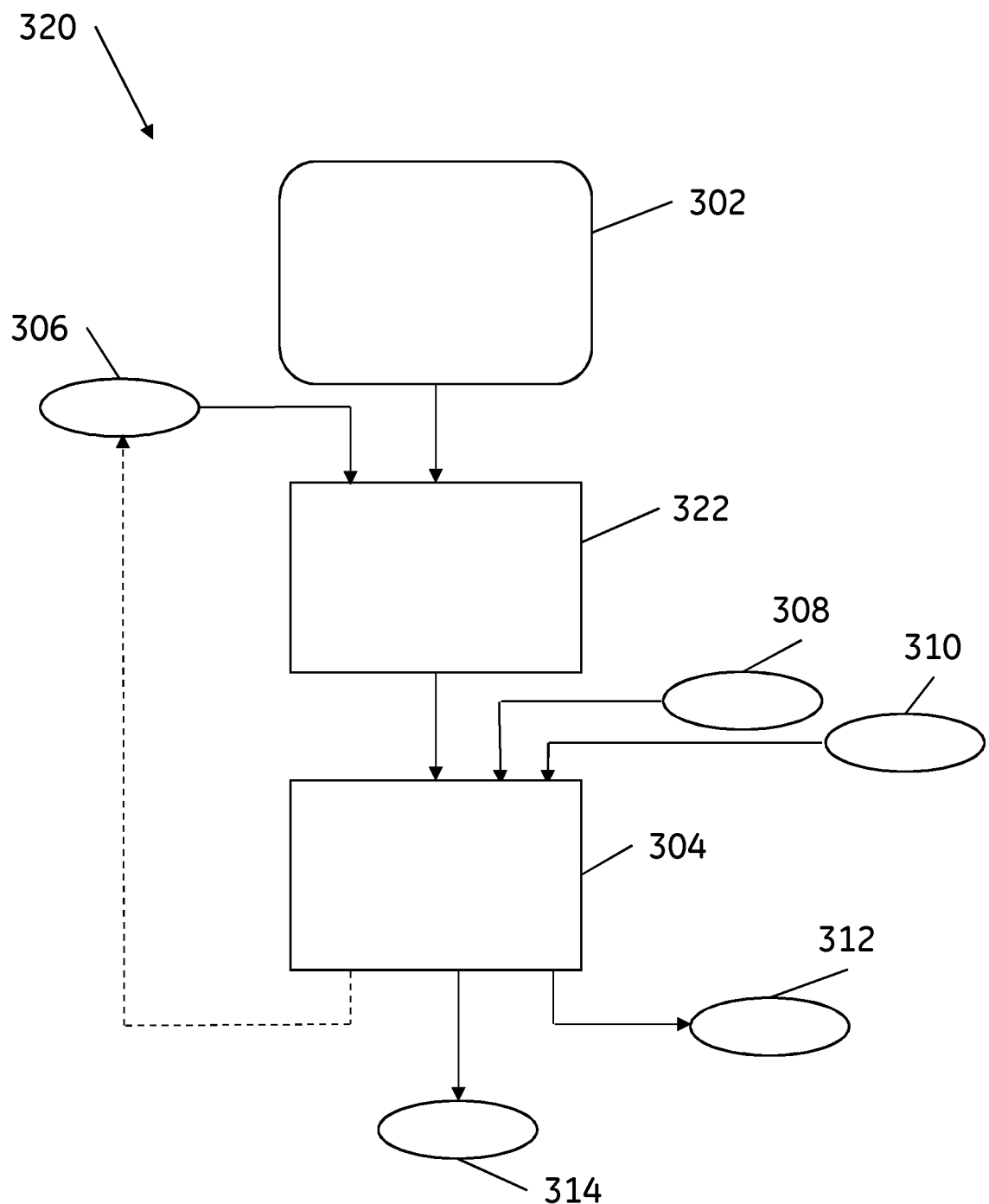
FIG. 5 shows an apparatus of the invention.

FIG. 5 shows an apparatus 320, comprising a bioreactor 302, a contactor 322 and a magnetic separator 304, where magnetic beads 306 can be added to the contactor 322 for incubation with a portion of cell culture conveyed from the bioreactor (step b)). During step c), wash liquid 308 is conveyed to the separator and during step d), eluent 310 is conveyed to the separator. An eluate 312 is recovered during step d) and spent cell culture and wash liquid is conveyed to a waste outlet 314 during step c). If the beads are cleaned and regenerated during step d), they can optionally be recycled to the bioreactor.

Figure 6:
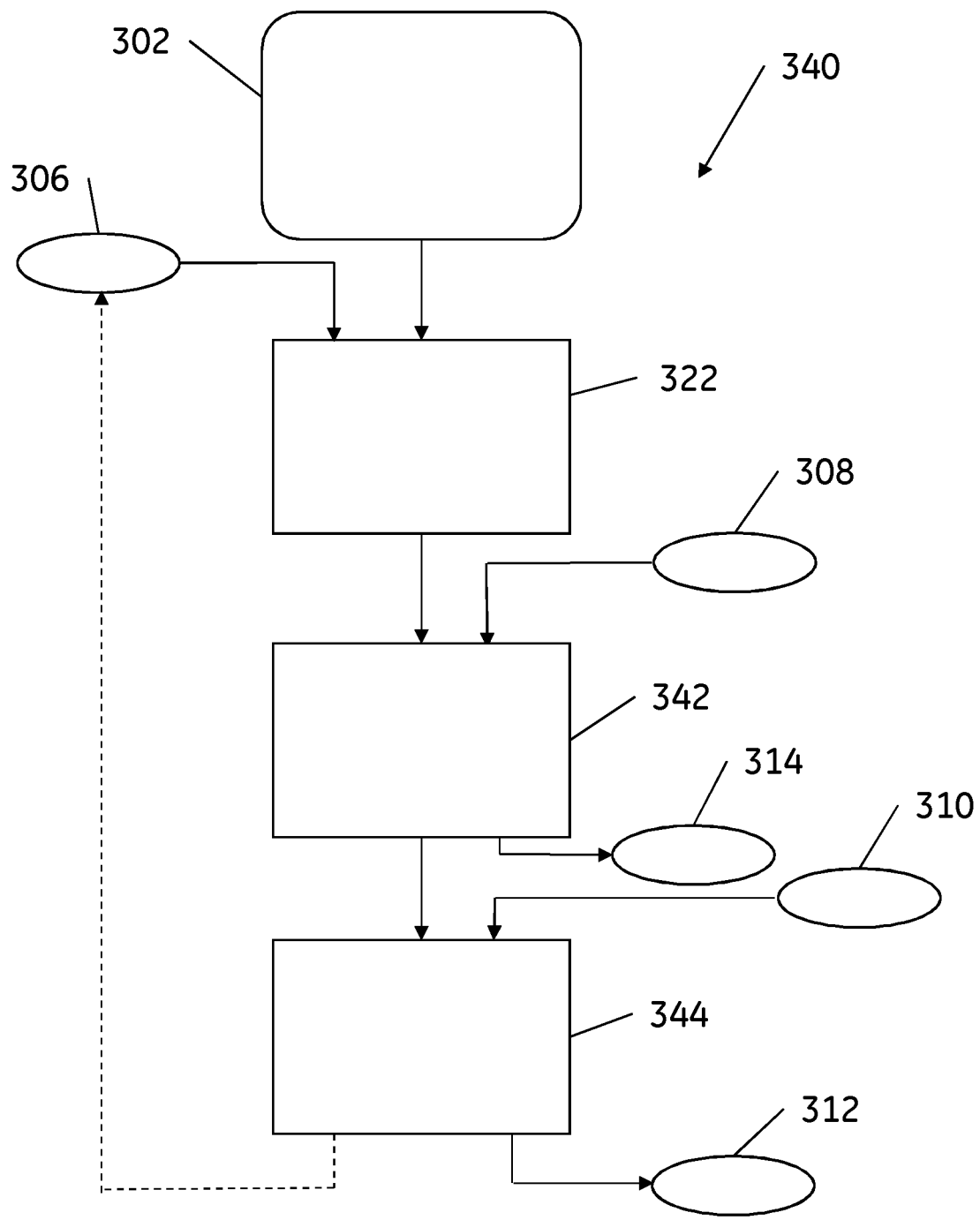
FIG. 6 shows an apparatus of the invention.

FIG. 6 shows an apparatus 340, comprising a bioreactor 302, a contactor 322, a washer separator 342 and an elution separator 344, where magnetic beads 306 can be added to the contactor 322 for incubation with a portion of cell culture conveyed from the bioreactor (step b)). The washing step c) is performed in the washer separator 342 and the elution step d) is performed in the elution separator 344. During step c), wash liquid 308 is conveyed to the washer separator 342 and during step d), eluent 310 is conveyed to the elution separator 344. An eluate 312 is recovered during step d) and spent cell culture and wash liquid is conveyed to a waste outlet 314 during step c). If the beads are cleaned and regenerated during step d), they can optionally be recycled to the bioreactor.

Figure 7:
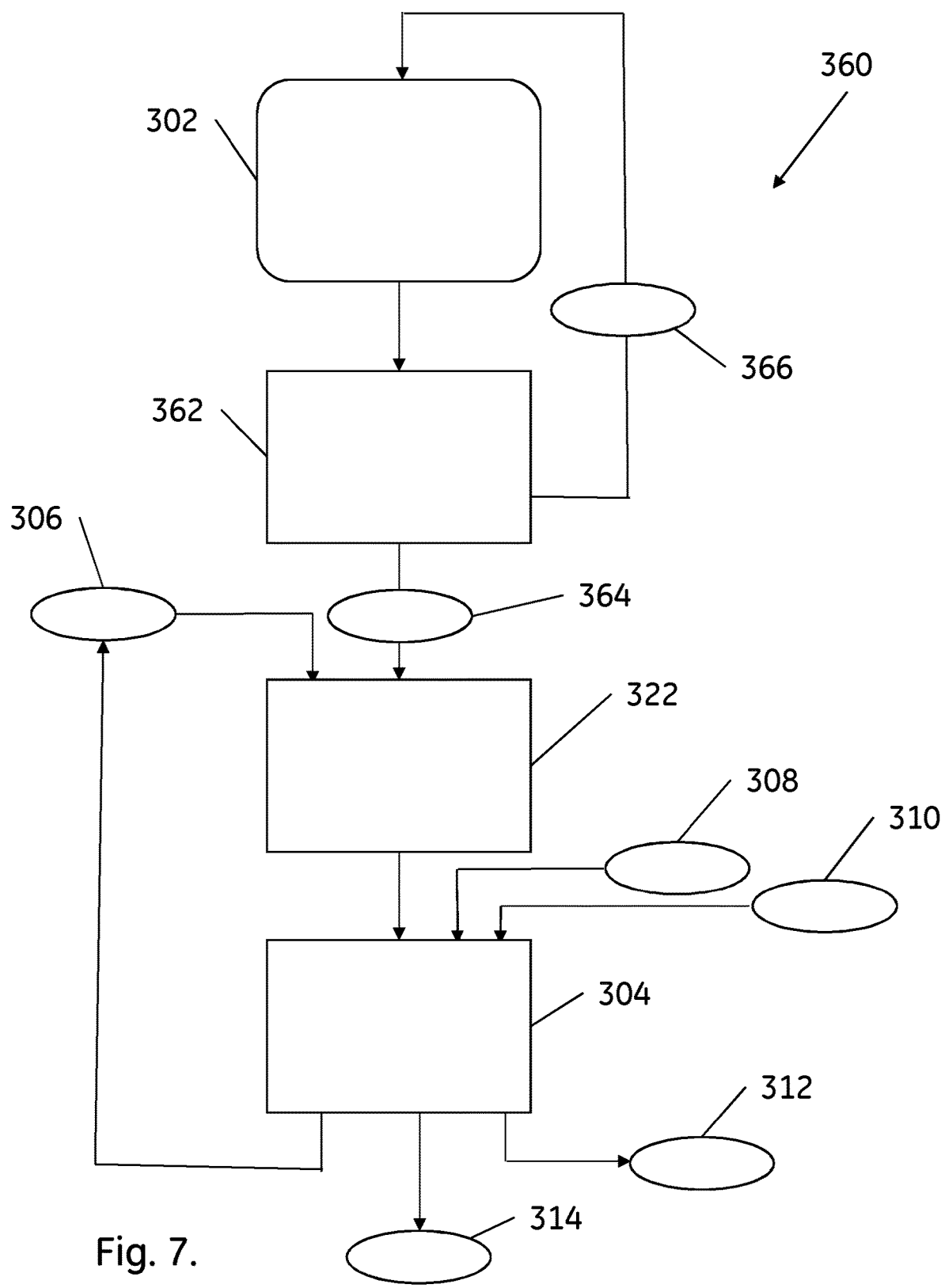
FIG. 7 shows an apparatus of the invention.

FIG. 7 shows a perfusion apparatus 360, comprising a bioreactor 302, a cell separation device 362, a contactor 322 and a magnetic separator 304, where magnetic beads 306 can be added to the contactor 322 for incubation with a portion of cell-depleted cell culture 364 conveyed from the cell separation device (step b)). The cell separation device can as described above be e.g. an inclined settler or an acoustic separation device 362, capable of separating cell culture conveyed from the bioreactor into a cell-depleted cell culture 364 and a cell concentrate 366 for recycling to the bioreactor. During step c), wash liquid 308 is conveyed to the separator and during step d), eluent 310 is conveyed to the separator. An eluate 312 is recovered during step d) and spent cell culture and wash liquid is conveyed to a waste outlet 314 during step c). The beads can suitably be cleaned and regenerated during step d), and then recycled to the bioreactor. Although FIG. 7 shows a single magnetic separator 304, it is equally possible to have two separate washer 342 and elution 344 separators as discussed above.

Figure 8:
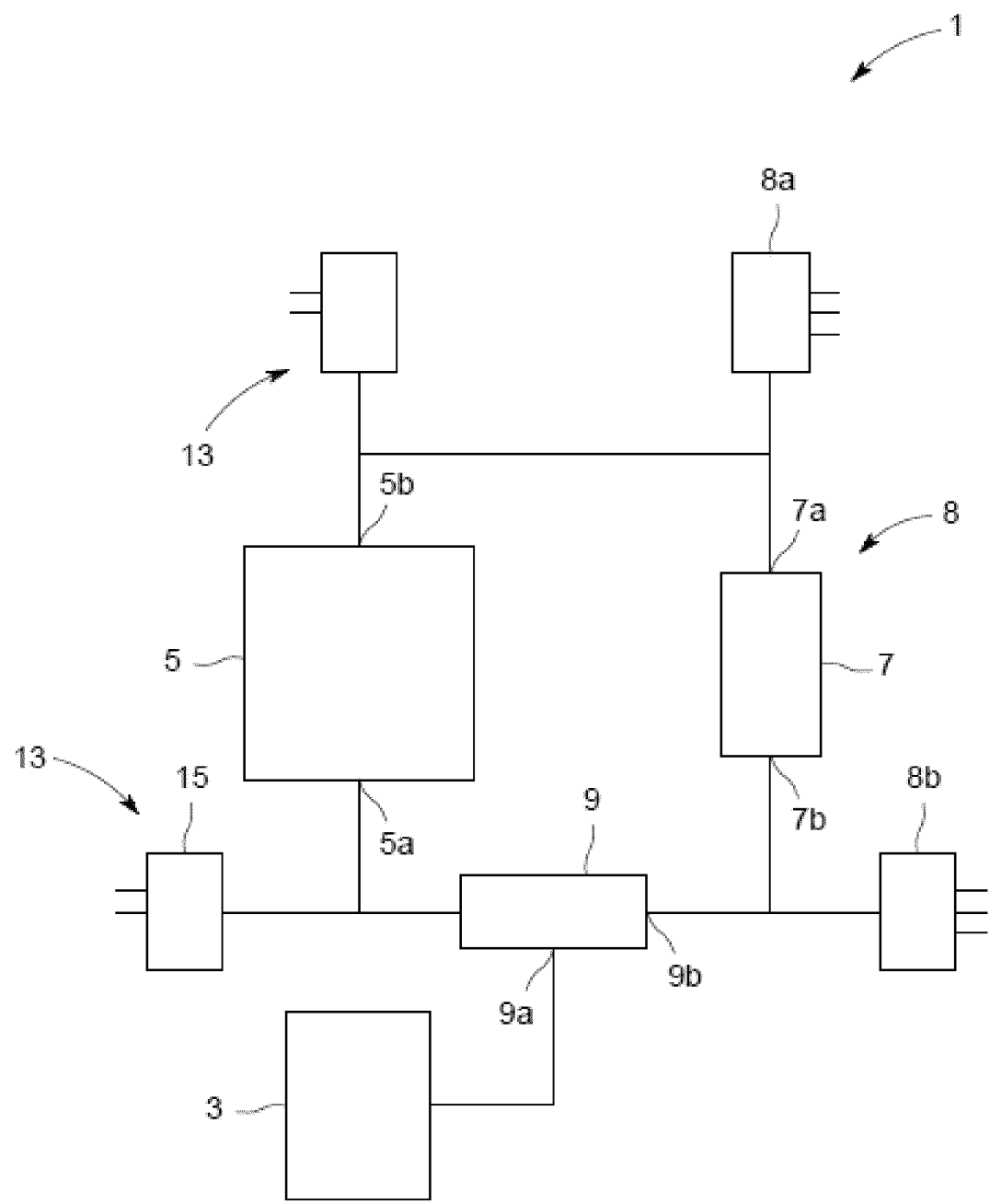
FIG. 8 shows an apparatus of the invention.

FIGS. 8, 9 and 10 show schematically three different possible apparatuses (also called separation systems) 1, 101, 201 according to the invention. Some features are the same and will be described only once and some features in one of the systems can also be used in one of the other systems. Common for the three shown systems 1, 101, 201 is that they comprise a magnetic separator 5, 105, 205. This could e.g. be a high gradient magnetic separator as described above or in U.S. Pat. No. 7,506,765. A magnetic separator, which may be a washer separator as discussed above, separates magnetic particles from a fluid. The magnetic separator 5; 105; 205 comprises an inlet 5a; 105a; 205a for receiving a cell culture (also called a feed from a cell culture) from e.g. a bioreactor 3; 103; 203 comprising the target biomolecule and for receiving magnetic beads comprising ligands capable of binding this biomolecule. The magnetic separator 5; 105; 205 is configured for separating said magnetic beads with the bound biomolecule from the rest of the cell culture/feed. The magnetic separator 5; 105; 205 comprises parts/elements of magnetic material inside the magnetic separator which parts attract the magnetic beads when a magnetic field is applied. The magnetic separator is configured for releasing the magnetic field when the magnetic beads are to be forwarded to an elution separator/elution cell 7; 107; 207 provided outside the magnetic separator and connected to the magnetic separator. The magnetic separator further comprises a washing arrangement 13; 113; 213 configured for washing out other components from the magnetic separator 5; 105; 205 than those magnetically bound to the parts of magnetic material. The washing arrangement 13; 113; 213 may comprise at least one wash buffer providing arrangement 15; 115; 215 connected to a pump and to the inlet 5a; 105a; 205a of the magnetic separator possibly via a contactor (also called a capturing cell) 9; 109; 209 and a wash buffer collection arrangement 17; 117; 217 connected to an outlet 5b; 105b; 205b of the magnetic separator. The washing arrangement 13; 113; 213 is configured for flowing washing buffer through the magnetic separator 5; 105; 205 for washing out other components of the feed than those bound to the magnetic parts.

All three apparatuses/separation systems 1; 101; 201 also comprise an elution separator (also called an elution arrangement) 8; 108; 208 comprising an elution cell 7; 107; 207. The elution cell comprises an elution cell inlet 7a; 107a; 207a in connection with an outlet 5b; 105b; 205b from the magnetic separator 5; 105; 205 for receiving said separated magnetic beads as a slurry with buffer from the magnetic separator. When forwarding the magnetic beads from the magnetic separator 5; 105; 205 to the elution arrangement buffer is suitably added to the magnetic separator for allowing the magnetic beads to be flowed to the elution arrangement 8; 108; 208.

The elution arrangement 8; 108; 208 is configured for eluting the biomolecule from the magnetic beads. Hereby the elution arrangement 8; 108; 208 comprises a buffer providing arrangement 8a; 108a; 208a connected to an elution cell inlet 7a; 107a'; 207a' and a collection arrangement 8b; 108b; 208b connected to an elution cell outlet 7b; 107b'; 207b'. The elution arrangement is configured for performing elution by providing elution buffer from the buffer providing arrangement and collecting eluate in the collection arrangement and possibly also performing strip and cleaning in place, CIP, by providing cleaning buffer from the buffer providing arrangement and collect waste in the collection arrangement and possibly also performing equilibration of the magnetic beads in the elution cell by providing equilibration buffer from the buffer providing arrangement.

In some embodiments the elution cell 107, 207 comprises two inlets 107a, 107a'; 207a, 207a' and two outlets 107b, 107b'; 207b, 207b'. Actually, also the elution cell 7 in the separation system shown in FIG. 8 can have two inlets and two outlets instead of only one inlet and one outlet and valves directing the fluids. And correspondingly the elution cells of the separation systems shown in FIGS. 9 and 10 could have only one inlet and one outlet as shown in FIG. 8. In the embodiment shown in FIG. 9 the elution cell 107 comprises an elution cell first outlet 107b for forwarding the magnetic beads for reuse in the magnetic separator 105 and an elution cell second outlet 107b' for collecting eluate and waste in a collection arrangement 108b.

In the embodiment shown in FIG. 10, the elution cell 207 comprises an elution cell first outlet 207b for forwarding the magnetic beads to a storage vessel 215 and an elution cell second outlet 207b' for collecting eluate and waste in a collection arrangement 208b. The separation system 201 shown in FIG. 10 is a system without a circulation and reuse of the magnetic beads. In this system, a cell culture 203 can be provided with the magnetic beads and connected to the separation system 201. Possibly all the content of the cell culture 203 could be provided to the magnetic separator 205. The magnetic beads are retrieved in the storage vessel 215 after the eluting of the biomolecules in the elution cell 207.

The elution cell 107; 207 comprises in the embodiment shown in FIGS. 9 and 10 an elution cell first inlet 107a; 207a for receiving magnetic beads from the magnetic separator 105; 205 and an elution cell second inlet 107a'; 207a' for receiving elution buffer, cleaning in place, CIP, buffer and equilibration buffer from a buffer providing arrangement 108a; 208a.

The elution cell 7; 107; 207 may comprise a retaining arrangement 502a-e for keeping the magnetic beads within the elution cell and allowing excess buffer to escape from the elution cell. In the embodiments shown in FIGS. 8 and 9, an elution cell outlet 7b; 107b is configured for forwarding the magnetic beads from the elution cell for reuse in the magnetic separator 5; 105; 205.

The apparatus/separation systems 1; 101 shown in FIGS. 8 and 9 comprises a contactor/capturing cell 9; 109 which is connected to the inlet 5a; 105a of the washer separator/magnetic separator 5; 105. The cell culture 203 in the embodiment shown in FIG. 10 can also be called a contactor/capturing cell 209 if magnetic beads are added to the cell culture 203. Another alternative would be to add magnetic beads directly to the magnetic separator 5; 105; 205 instead. Separate addition of cell culture and magnetic beads directly into the magnetic separator is possible for all the embodiments and should be covered by this invention.

The capturing cells 9; 109 shown in FIGS. 8 and 9 may comprise a cell culture inlet 9a; 109a for receiving a cell culture/feed from a cell culture 3; 103 and at least one magnetic bead inlet 9b; 109b; 109c for receiving magnetic beads. The capturing cell 9; 109 is configured for mixing the feed from the cell culture and the magnetic beads thus allowing the specific biomolecule to bind to the magnetic beads before forwarding it to the magnetic separator 5; 105.

In the separation systems 1; 101; 201 according to the invention a new portion of feed from the cell culture 3; 103; 203 and magnetic beads can be provided into the magnetic separator 5; 105; 205 while a previous portion is in the elution cell 7; 107; 207. Hereby at least two portions of magnetic beads can be used in the separation system simultaneously and processes for separating biomolecules can be made more effective.

In the embodiments shown in FIGS. 8 and 9 the magnetic beads are circulating in the separation system 1; 101 and still a new portion of feed from the cell culture 3; 103 and magnetic beads can be provided into the magnetic separator 5; 105 while one previous portion is in the elution cell 7; 107 and one previous portion is in a capturing cell 9; 109. Hereby three portions of magnetic beads are circulating in the separation system 1; 101; 201.

For all the embodiments shown in FIGS. 8-10 the cell culture 3; 103; 203, the magnetic separator 5; 105; 205 and the elution arrangement 8; 108; 208 can be connected by pre-sterilized, flexible tubing and aseptic connectors. Furthermore, the elution cell can be pre-sterilized and disposable. A closed and sterile separation system for single use can hereby be provided.

The separation system 101 shown in FIG. 9 comprises further an intermediate cell 111 connected to an elution cell outlet 107b and configured for receiving the magnetic beads form the elution cell. The intermediate cell 111 is configured for forwarding the magnetic beads for possible reuse in the magnetic separator 5; 105; 205. The intermediate cell 111 comprises in one embodiment a draining arrangement for removing excess buffer from the intermediate cell 111. Such a draining arrangement could also or instead be provided to the capturing cell 9, 109 of the systems in FIGS. 8 and 9.

The methods of the invention can also be carried out in a separation apparatus 500 as illustrated in FIG. 17. Here a bioreactor 502 is fluidically connected via a feed line 525 to a fluidics control system 501, exemplified in detail in FIG. 18. The fluidics control system is further fluidically connected to a first magnetic separator or combined contactor-magnetic separator 505, e.g. via first separator input line 530 and first separator output line 540. A second magnetic separator or combined contactor-magnetic separator 507 may also be fluidically connected to the fluidics control system, e.g. via second separator input line 535 and second separator output line 545. Further, a first 510, second 515 and third 520 buffer vessel may be fluidically connected to the fluidics control system via a first 550, second 555 and third 560 buffer line. Output from the fluidics control system may be directed via a product line 565 and/or via waste line 570. The fluidics control system 501 suitably comprises one or more manifolds 582, at least one pump 586, valves 584 and tubing 592, configured to convey a cell culture from bioreactor 502 via feed line 525 to either first magnetic separator 505 via first separator input line 530 or to second magnetic separator 507 via second separator input line 535. The fluidics control system is further configured to convey liquid from first 505 or second 507 magnetic separator via first/second output line 540,545 to either waste line 570 or to product line 565. One or more buffers may be conveyed from first 510, second 515 and/or third 529 buffer vessel via first/second/third buffer line 550,555,560 to either first 505 or second 507 magnetic separator via first/second separator input line 530,535. The fluidics control system may comprise one or more sensors 588, configured to measure properties such as flow rate, pressure, pH, conductivity, temperature, optical transmission etc. for liquids conveyed through the tubing 592. A control unit 590 is signally connected (connections not shown) to the pump, valves and sensors and configured to control the flow of liquids through the fluidics control system. The control unit may also be signally connected to the first and second magnetic separators via signal connections 575,580 and configured to control agitation and/or magnetic fields in the magnetic separators. A chromatography system for single flowpaths, like e.g. ÄKTA ready (GE Healthcare) may be used as the fluidics control system 501, with some added functionality for controlling the magnetic separators.

In separation apparatus 500, a cell culture from bioreactor 502 can be fed into one of the magnetic separators or combined contactors-magnetic separators 505,507, containing magnetic beads as discussed above, allowing a target biomolecule, such as an immunoglobulin, to bind to the beads. The beads are then retained by a magnetic field while the now depleted cell culture is conveyed to waste line 570. Wash buffer is conveyed from e.g. first buffer vessel 510 to the magnetic separator and, with the magnetic field switched off, incubated with the magnetic beads. After switching on the magnetic field and conveying the wash buffer to waste line 570, an elution buffer is conveyed from e.g. second buffer vessel 515 to the separator and, with the magnetic field switched off, incubated with the magnetic beads to elute the target biomolecule/immunoglobulin. The elution buffer with eluted target biomolecule/immunoglobulin is separated from the beads by switching on the magnetic field and conveyed to product line 565 for further processing or intermediate storage. With two magnetic separators it is possible to process feed in one of the separators simultaneously with washing and/or elution in the other magnetic separator, allowing efficient cycling of the separation steps when harvesting from a large bioreactor, requiring e.g. 5-10 load cycles in the bags. After elution, the magnetic beads can suitably be regenerated by incubation with a regeneration buffer from e.g. third buffer vessel 520. The beads can also, after regeneration, be equilibrated with an equilibration buffer, which can be the wash buffer from e.g. first buffer vessel 510. Suitably, feed incubation, washing, elution, regeneration or equilibration in one of the separators is carried out simultaneously with another of these steps in the other separator to allow for higher throughput. It is further contemplated that three (or even four) independently operable magnetic separators or combined contactors-magnetic separators (the third/fourth separators not shown) can be used to simultaneously carry out different steps to further increase the throughput. The fluidics control system may in such applications comprise two or more pumps and more complex manifold/valve systems to allow for simultaneous conveying of liquids into and out of the different separators. With multiple separators it is also possible to convey the cell culture feed, after depletion in a first separator with magnetic beads, to a second separator with magnetic beads to bind any target biomolecule/immunoglobulin which did not bind in the first separator. This will improve the recovery of the target biomolecule, particularly in the case where the ligand-target adsorption isotherm is comparatively shallow.

The magnetic separators/combined contactors-magnetic separators may suitably be flexible bags 405 on rocking platforms 410 as illustrated in FIGS. 11 and 12 and discussed above. The separator shown in FIG. 19a) with an electromagnet 431 beneath the bag bottom surface 436, signally connected 575 to the control unit 590, can be particularly suitable. The rocking platform may also be equipped with load cells 448, signally connected 575 to the control unit 590, to allow for feedback control of the amount of liquid in the bag. The bags may also comprise one or more sensors (not shown) for sensing e.g. temperature, pH, conductivity, target biomolecule concentration etc. Further, the outlets from the bags may be equipped with air sensors (not shown) to detect when the bags have been emptied and to prevent suction of air into the pump(s). The bags may be supplied with a suitable amount of magnetic beads inside the bag, or the beads may be introduced into the bags, e.g. via an aseptic port in the bag, before start of the process. The bags can advantageously be constructed as shown in FIGS. 19b) and c), with a top film 601 and a bottom film 603 welded to a spacer frame 607 to form a bag 605. If the top and bottom films are welded directly to each other as in standard pillow-type bags, a narrow wedge-shaped space is formed near the weld, where beads may be entrapped. This is avoided by the use of the spacer frame 607, which may e.g. have a thickness of 2-20 mm. The spacer frame is suitably made from a material which is weldable with the top and bottom films, e.g. polyethylene when polyethylene films are used. As shown in FIGS. 19b) and c), inlet and outlet ports 609 may also be formed in the spacer frame 607, particularly if it has a thickness 5-20 mm, and they may optionally be equipped with screens 613 to prevent any stray beads from exiting the bag with the output streams. The screens should preferably be designed to retain beads but let cells pass. Alternatively, the screens can be replaced with small magnetic separators.

Separation apparatus 500 can suitably be configured with single use wetted components. The flexible bags 405 can be single use bags, lines 525,530,535,540,545,550,555,560, 565,570, as well as tubing 592 can be single use plastic or elastomeric tubing, valves 584 can be e.g. pinch valves, the pump(s) 586 can be peristaltic pump(s), e.g. membrane or centrifugal pump(s) with single use pump head(s) and the sensor(s) 588 may have a single use wetted part signally/ physically connected to a reusable part. The buffer vessels 510,515,520 may e.g. be single use flexible bags and/or the bioreactor 502 may comprise a single use flexible bag bioreactor vessel. The wetted components may be supplied as one or more pre-assembled flow kits comprising tubing, connectors, bags, wetted parts of sensors and/or single use pump heads. Such flow kits may advantageously be pre-sterilized, e.g. by gamma irradiation. The flow kits may comprise aseptic connectors for aseptic connection of different flow kits with each other and/or with other components.

EXAMPLES

Example 1

Magnetic Agarose Beads

A hot (74° C.) dispersion of 80 g magnetite particles in 836 g aqueous agarose solution (800 g water and 36 g agarose) was emulsified in a hot (60° C.) solution of 50 g ethyl cellulose emulsifier in 1120 ml toluene, using an overhead agitator in a thermostated cylindrical glass vessel. Samples were removed during the emulsification for particle size measurement using a Malvern Mastersizer laser diffraction instrument. The agitation was continued until a target volume-weighted median droplet diameter of 62 micrometers had been reached. At that point the agitator rpm was decreased and the emulsion was cooled to 22° C., in order to obtain solid agarose gel beads with embedded magnetite particles. The beads were then sedimentation washed 5 times with 95% ethanol and 5 times with distilled water. The magnetite powder used was obtained from Aldrich (article #31,006-9) and had a volume-weighted median particle diameter (d50,v) of 1.5 micrometers, with 10 and 90% quantiles of d10,v=0.7 micrometers and d90,v=4.0 micrometers.

1.0 liters of sedimented beads were crosslinked with epichlorohydrin by the following procedure: Add water to a total volume of 1.2 liters and dissolve 149 g sodium sulfate, 10.5 ml 50% NaOH and 1.0 g sodium borohydride in the mixture. Increase the temperature to 47° C. and add 124 ml epichlorohydrin and 85 ml 50% NaOH under agitation during 6 h. Cool to room temperature and neutralize with acetic acid. Wash on a glass filter with 6×1 liter distilled water. Sieve the beads between 37 micrometer and 100 micrometer sieving cloths.

Figure 2:
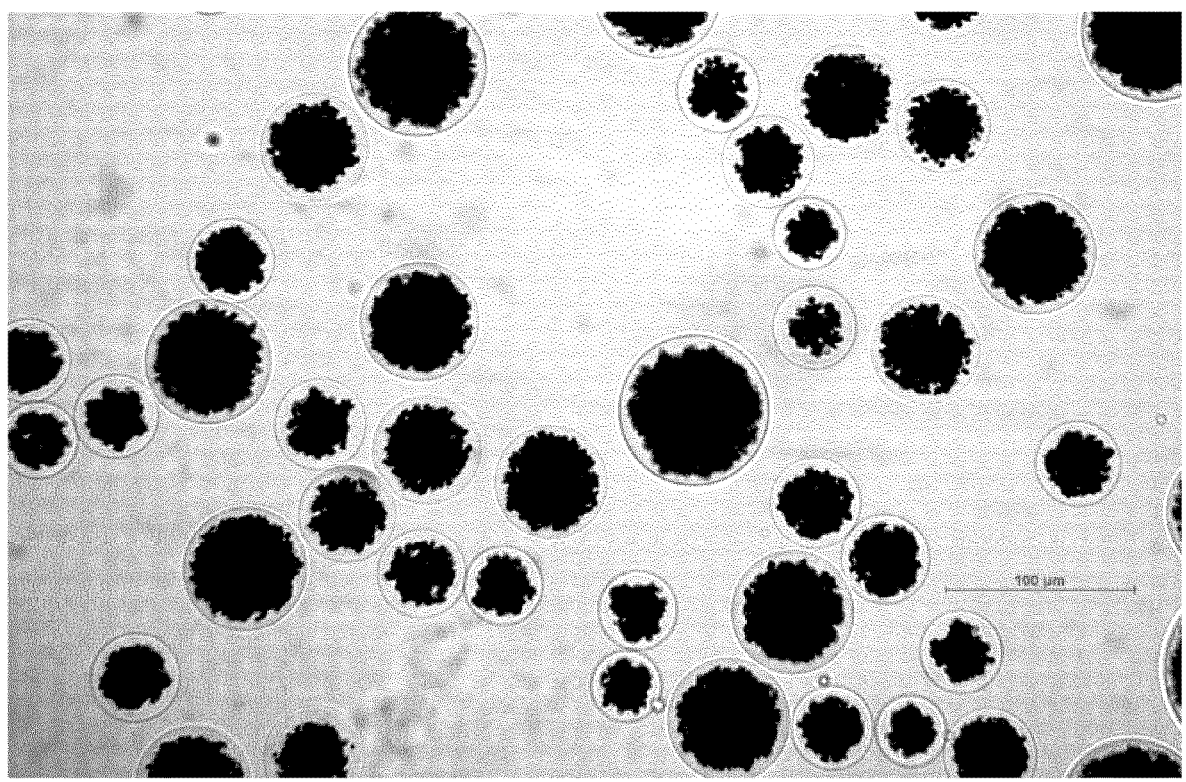
FIG. 2 shows a photomicrograph of magnetic agarose beads according to the invention.

The particle size distribution of the crosslinked beads was determined in a Malvern Mastersizer laser diffraction instrument and the volume-weighted median particle diameter (d50,v) was found to be 65 micrometers. Photographs of the beads are shown in FIG. 2 and show that the magnetite particles (black) are located primarily, or even exclusively, in a central region of each bead.

The beads can be described as having a porous agarose gel phase with 4.3 wt. % agarose concentration and solid magnetite particles embedded in the agarose gel phase. The average content of magnetite in the beads is 9.6 wt. % (1.8 vol %) and the density of the beads is 1.1 g/cm$^3$ (magnetite having a density of 5.2 g/cm$^3$).

Coupling of Ligand to the Beads

The ligand was a tetrameric alkali-stabilized variant of Protein Z with a C-terminal cysteine (SEQ ID NO: 2), known to have an affinity constant $k_{off}/k_{on}$ of 700 pM for IgG.

50 ml magnetic beads were washed with 10 gel volumes distilled water on a glass filter. The beads were mixed with 15 ml distilled water and 4 g NaOH (0.1 mol) in a 250 ml flask with an agitator. The temperature was adjusted to 27+/−2° C. in a water bath. 8 ml epichlorohydrin (0.1 mol) was added under vigorous agitation (about 250 rpm) during 90+/−10 minutes. The reaction was allowed to continue for another 80+/−10 minutes and the beads were then washed with >10 gel volumes distilled water on a glass filter until neutral pH was reached. These activated beads were used directly for coupling as below.

To 20 mL of ligand solution (50 mg/mL) in a 50 ml Falcon tube, 169 mg NaHCO$_3$, 21 mg Na$_2$CO$_3$, 175 mg NaCl and 7 mg EDTA, was added. The Falcon tube was placed on a roller table for 5-10 min, and then 77 mg of DTE was added. Reduction proceeded for >45 min. The ligand solution was then desalted on a PD10 column packed with Sephadex G-25. The ligand content in the desalted solution was determined by measuring the 276 nm UV absorption.

The activated beads were washed with 3-5 GV {0.1 M phosphate/1 mM EDTA pH 8.6} and the ligand was then coupled according to the method described in U.S. Pat. No. 6,399,750, hereby incorporated by reference in its entirety, although with 20 mg ligand added per mL beads. All buffers used in the experiments had been degassed by nitrogen gas for at least 5-10 min.

After immobilization, the beads were washed 3×GV with distilled water. The beads+1 GV {0.1 M phosphate/1 mM EDTA/10% thioglycerol pH 8.6} was mixed and left on a shaking table at room temperature overnight. The beads were then washed alternately with 3×GV {0.1 M TRIS/0.15 M NaCl pH 8.6} and 0.5 M HAc and then 8-10×GV with distilled water.

Characterization of the Beads with Ligands

Ligand Content

Bead samples were sent to an external laboratory for amino acid analysis and the ligand content was calculated from the total amino acid content to be 21.3 mg/ml beads.

Dynamic Binding Capacity 2 ml of resin was packed in TRICORN™ 5 100 columns. The breakthrough capacity was determined with an ÄKTA-Explorer 10 system at a residence time of 6 minutes (0.33 ml/min flow rate). Equilibration buffer was run through the bypass column until a stable baseline was obtained. This was done prior to auto zeroing. Sample was applied to the column until a 100% UV signal was obtained. Then, equilibration buffer was applied again until a stable baseline was obtained.

Sample was loaded onto the column until a UV signal of 85% of maximum absorbance was reached. The column was then washed with 5 column volumes (CV) equilibration buffer at flow rate 0.5 ml/min. The protein was eluted with 5 CV elution buffer at a flow rate of 0.5 ml/min. Then the column was cleaned with 0.5M NaOH at flow rate 0.2 ml/min and re-equilibrated with equilibration buffer.

For calculation of breakthrough capacity at 10%, the equation below was used. That is the amount of IgG that is loaded onto the column until the concentration of IgG in the column effluent is 10% of the IgG concentration in the feed.

$$q_{10\%} = \frac{C_0}{V_C}\left[V_{app} - V_{sys} - \int_{V_{sys}}^{V_{app}} \frac{A(V) - A_{sub}}{A_{100\%} - A_{sub}} * dv\right]$$

$A_{100\%}$=100% UV signal;
$A_{sub}$=absorbance contribution from non-binding IgG subclass;
$A(V)$=absorbance at a given applied volume;
$V_c$=column volume;
$V_{app}$=volume applied until 10% breakthrough;
$V_{sys}$=system dead volume;
$C_0$=feed concentration.

The dynamic binding capacity (DBC) was calculated for 5, 10 and 80% breakthrough and found to be: Qb 5%=69 mg/ml, Qb 10%=72 mg/ml and Qb 80%=100 mg/ml.

Adsorption Isotherm

An adsorption isotherm for the IgG antibody directly from the cell culture on the beads was determined using batch adsorption on 20-200 microliter bead aliquots in 1.5 mL test tubes with 1 h incubation time. The antibody concentration in the supernatant was determined and the adsorbed amount was calculated from the differential concentration after and before incubation. The adsorbed amount vs. equilibrium supernatant concentration was plotted as the adsorption isotherm (FIG. 13) and the Langmuir equation $q=q_m c/(K+c)$ was fitted to the data, where q is the bound amount (mg/ml), c is the equilibrium solution concentration (mg/ml), K is a dissociation constant (mg/ml) and $q_m$ is the maximum binding capacity (mg/ml). The calculated parameters were $q_m$ (max binding capacity)=87 mg/ml and K (dissociation constant)=0.06 mg/ml. This shows that the isotherm is highly favorable with a remarkably strong binding of the antibody to the beads.

Cell Culture

A CHO cell culture expressing an IgG monoclonal antibody was used for the evaluations. Evaluation samples were withdrawn from the culture during two consecutive days. The first day, the antibody titer was 2.2 mg IgG/ml and the cell density $1.2 \times 10^7$ cells/ml. The second day, the titer was 2.6 mg IgG/ml, with cell density $1.8 \times 10^7$ cells/ml. In both cases, the cell viability was >90%.

High Gradient Magnetic Field Separator (HGMS)

An Andritz high-gradient magnetic separator with a rotor-stator design (Andritz Separation, Germany) was used for washing and elution in the evaluation tests. The separator design is disclosed in U.S. Pat. No. 7,506,765 (hereby incorporated by reference in its entirety) and comprises a stator with parallel perforated magnetizable circular disks and a rotor with perforated rotating disks interspersed with the stator disks. When the disks are magnetized with an electromagnet, the beads will adhere to the disks and when the magnetic field is removed, the beads can be redispersed through rotation of the rotor disks. The disks are enclosed in a flow-through chamber of 980 ml volume, connected to a peristaltic pump capable of delivering a flow rate of 2.7 liters/minute. Up to 600 ml magnetic beads can be retained in the chamber.

Evaluation

About 2-3 liters of cell culture were mixed with about 200 ml magnetic beads in a 3 L plastic beaker and incubated for 60 minutes. The cell culture and the beads were then conveyed to the HGMS chamber and the magnetic field applied to retain the beads. Three wash cycles with PBS buffer and one with distilled water were then performed, each cycle involving filling the chamber with liquid, redispersing the beads by removing the magnetic field and rotating the rotor disks and re-applying the magnetic field and draining the chamber. After the last wash cycle, three elution cycles were then performed, in the same way as the wash cycles, but with 100 mM Na-acetate pH 2.9 as the elution buffer. The three eluates were pooled and analyzed, while the beads were cleaned with three cleaning cycles using 0.1 M NaOH as the cleaning liquid. Finally, the beads were reequilibrated with three cycles of PBS buffer and the beads were then pumped back to the flexible plastic bag for repetition of the experiment with a new aliquot of the cell culture. The total time of the wash, elution, cleaning and reequilibration steps was 60 min.

Evaluation Results

Five evaluation cycles with the same bead sample were performed, using the conditions of Table 1.

TABLE 1

Evaluation cycles

| Cycle No. | Culture volume (L) | Bead volume (mL) | Titer (mg IgG/mL) | Loading (mg IgG/mL beads) | Volume transferred to HGMS (L) |
|---|---|---|---|---|---|
| 1 | 2.77 | 200 | 2.2 | 30 | 2.26 |
| 2 | 2.27 | 200 | 2.2 | 25 | 2.26 |
| 3 | 1.98 | 200 | 2.2 | 23 | 3.00 |
| 4 | 2.80 | 212 | 2.6 | 34 | 2.49 |
| 5 | 2.30 | 170 | 2.6 | 35 | 3.04 |

The cells were stained for viability testing during the incubation with the beads and no effects on the viability could be observed. The viability before and after 30 and 60 min incubation was constant 93.5-93.7%. This means that it is possible to cultivate the cells in the presence of the magnetic beads to capture the immunoglobulin during ongoing cultivation.

The IgG uptake by the beads as a function of incubation time was measured and is shown in FIG. 14. Equilibrium was reached after approx. 20 min.

The antibody yield in the three eluate fractions is shown in FIG. 15. The total yield in the eluate pools and the antibody purity as determined by size exclusion chromatography (SEC) are shown in Table 2. An example SEC chromatogram of an eluate is shown in FIG. 16.

TABLE 2

Evaluation results

| Cycle No. | Antibody yield (%) | Purity by SEC (%) |
|---|---|---|
| 1 | 88 | 96.5 |
| 2 | 94 | 95.4 |
| 3 | 87 | 95.6 |
| 4 | 86 | 96.0 |
| 5 | 85 | 96.9 |

Productivity

An overview of productivity estimates based on the experiments is shown in Table 3.

TABLE 3

Productivity estimates

| Parameter | Experiments | Max output | Realistic output |
|---|---|---|---|
| Bead capacity utilized | 35 mg/mL | 80 mg/mL | 60 mg/mL |
| Yield | 90% | 80% | 90% |
| Bead volume | 200 mL | 500 mL | 400 mL |
| Volume of feed per cycle | 2.3 L | 13.3 L | 8.0 L |
| Productivity | 6.2 g/h | 32 g/h | 22 g/h |
| Volume of feed per 8 cycles | 18 L | 106 L | 64 L |
| Productivity | 50 g/day | 256 g/day | 176 g/day |

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. All patents and patent applications mentioned in the text are hereby incorporated by reference in their entireties as if individually incorporated.

The invention claimed is:

1. A method of separating a target biomolecule from a cell culture, comprising the steps of:
    a) providing a plurality of magnetic beads capable of binding said target biomolecule;
    b) contacting said plurality of magnetic beads with a cell culture comprising a target biomolecule, to bind said target biomolecule to said beads;
    c) retaining said magnetic beads with a magnetic field in a high gradient magnetic field separator (HGMS) and washing said beads with a washing liquid; and
    d) eluting said magnetic beads with an eluent to desorb said target biomolecule from said beads and recovering said target biomolecule in an eluate,
        wherein said contacting of said plurality of magnetic beads with said cell culture is performed in a flexible bag mounted on a tray adapted to rock around a horizontal axis, wherein step b) is performed in a bioreactor, and wherein said bioreactor is said flexible bag.

2. The method of claim 1, wherein before step c), said magnetic beads are conveyed to said HGMS.

3. The method of claim 1, wherein step d) is performed in a second high gradient magnetic field separator (HGMS) or in the same HGMS.

4. The method of claim 3, wherein both steps c) and d) are performed in the same HGMS.

5. The method of claim 3, wherein the HGMS of step c) is a washer HGMS and step d) is performed in an elution HGMS.

6. The method of claim 1, wherein after step d), said magnetic beads are cleaned, reequilibrated and reused in a bioreactor.

7. The method of claim 1, wherein said cell culture comprises at least 1 mg/ml target biomolecule.

8. The method of claim 1, wherein said eluate is applied directly to a chromatography column.

9. The method of claim 1, wherein step c) comprises a sequence of:
    i) removing said magnetic field;
    ii) resuspending said beads;
    iii) contacting said beads with a portion of washing liquid;

iv) retaining said beads with a magnetic field; and
v) removing washing liquid from said retained beads.

10. The method of claim 1, wherein in step d) said beads are retained with a magnetic field.

11. The method of claim 1, wherein step c) and optionally step d) are performed in said bioreactor.

12. The method of claim 11, wherein a portion of said bioreactor is configured for magnetic retention of said magnetic beads.

13. The method of claim 1, wherein said tray comprises at least one magnet or magnet holder.

14. The method of claim 1, where said magnetic beads are presterilized.

15. The method of claim 14, wherein said magnetic beads are supplied dry.

16. The method of claim 14, wherein said magnetic beads are conveyed from a presterilized bead container via presterilized tubing and one or more aseptic connectors to the bioreactor, to a magnetic separator or to a contactor.

17. The method of claim 1, wherein after step d), said magnetic beads are regenerated and recirculated to the bioreactor and steps b)-d) are repeated.

18. The method of claim 17, wherein said magnetic beads are sterilized before recirculation to the bioreactor.

19. The method of claim 1, wherein cells are cultivated in the bioreactor in the presence of said magnetic beads.

20. The method of claim 1, wherein in step b) said cell culture is an unclarified or cell-depleted cell culture.

21. The method of claim 20, wherein said unclarified or cell-depleted cell culture comprises at least 1 mg/ml target biomolecule.

22. The method of claim 1, wherein said target biomolecule is an immunoglobulin, and wherein said magnetic beads comprise a porous matrix and one or more magnetic particles embedded in said matrix, wherein said matrix comprises a porous polymer and at least 10 mg/ml Fc-binding proteinaceous ligands covalently coupled to said porous polymer.

23. The method of claim 22, wherein said ligands comprise one or more alkali-stabilized mutants of SpA Fc-binding domains.

24. A method of separating a target biomolecule from a cell culture, comprising the steps of:
    a) providing a plurality of magnetic beads capable of binding said target biomolecule;
    b) contacting said plurality of magnetic beads with a cell culture comprising a target biomolecule, to bind said target biomolecule to said beads;
    c) retaining said magnetic beads with a magnetic field in a high gradient magnetic field separator (HGMS) and washing said beads with a washing liquid; and
    d) eluting said magnetic beads with an eluent to desorb said target biomolecule from said beads and recovering said target biomolecule in an eluate,
    wherein said contacting of said plurality of magnetic beads with said cell culture is performed in a flexible bag mounted on a tray adapted to rock around a horizontal axis, wherein step b) is performed in a contactor, and wherein said contactor is said flexible bag.

25. The method of claim 24, wherein, after step d), said beads are recirculated to said contactor.

* * * * *

SEQUENCE LISTING

```
<160> NUMBER OF SEQ ID NOS: 2

<210> SEQ ID NO 1
<211> LENGTH: 52
<212> TYPE: PRT
<213> ORGANISM: Escherichia coli

<400> SEQUENCE: 1

Lys Glu Gln Gln Asn Ala Phe Tyr Glu Ile Leu His Leu Pro Asn Leu
1               5                   10                  15

Thr Glu Glu Gln Arg Asn Ala Phe Ile Gln Ser Leu Lys Asp Asp Pro
            20                  25                  30

Ser Gln Ser Ala Asn Leu Leu Ala Glu Ala Lys Lys Leu Asn Asp Ala
        35                  40                  45

Gln Ala Pro Lys
    50
```

-continued

```
<210> SEQ ID NO 2
<211> LENGTH: 237
<212> TYPE: PRT
<213> ORGANISM: Escherichia coli

<400> SEQUENCE: 2

Ala Gln Gly Thr Val Asp Ala Lys Phe Asp Lys Glu Gln Gln Asn Ala
1               5                   10                  15

Phe Tyr Glu Ile Leu His Leu Pro Asn Leu Thr Glu Glu Gln Arg Asn
                20                  25                  30

Ala Phe Ile Gln Ser Leu Lys Asp Asp Pro Ser Gln Ser Ala Asn Leu
            35                  40                  45

Leu Ala Glu Ala Lys Lys Leu Asn Asp Ala Gln Ala Pro Lys Val Asp
    50                  55                  60

Ala Lys Phe Asp Lys Glu Gln Gln Asn Ala Phe Tyr Glu Ile Leu His
65                  70                  75                  80

Leu Pro Asn Leu Thr Glu Glu Gln Arg Asn Ala Phe Ile Gln Ser Leu
                85                  90                  95

Lys Asp Asp Pro Ser Gln Ser Ala Asn Leu Leu Ala Glu Ala Lys Lys
                100                 105                 110

Leu Asn Asp Ala Gln Ala Pro Lys Val Asp Ala Lys Phe Asp Lys Glu
            115                 120                 125

Gln Gln Asn Ala Phe Tyr Glu Ile Leu His Leu Pro Asn Leu Thr Glu
    130                 135                 140

Glu Gln Arg Asn Ala Phe Ile Gln Ser Leu Lys Asp Asp Pro Ser Gln
145                 150                 155                 160

Ser Ala Asn Leu Leu Ala Glu Ala Lys Lys Leu Asn Asp Ala Gln Ala
                165                 170                 175

Pro Lys Val Asp Ala Lys Phe Asp Lys Glu Gln Gln Asn Ala Phe Tyr
                180                 185                 190

Glu Ile Leu His Leu Pro Asn Leu Thr Glu Glu Gln Arg Asn Ala Phe
            195                 200                 205

Ile Gln Ser Leu Lys Asp Asp Pro Ser Gln Ser Ala Asn Leu Leu Ala
    210                 215                 220

Glu Ala Lys Lys Leu Asn Asp Ala Gln Ala Pro Lys Cys
225                 230                 235
```